US010633639B2

(12) United States Patent
Goldbaum et al.

(10) Patent No.: US 10,633,639 B2
(45) Date of Patent: Apr. 28, 2020

(54) **CHIMERAS OF *BRUCELLA* LUMAZINE SYNTHASE AND BETA SUBUNIT OF $AB_5$ TOXINS**

(71) Applicants: INMUNOVA S.A., Ciudad Autónoma de Buenos Aires (AR); CONSEJO NACIONAL DE INVESTIGACIONES CIENTIFICAS Y TECNICAS, Ciudad Autónoma de Buenos Aires (AR)

(72) Inventors: Fernando Alberto Goldbaum, Ciudad Autonoma de Buenos Aires (AR); Vanesa Zylberman, Ciudad Autonoma de Buenos Aires (AR); Patricio Oliver Craig, Ciudad Autonoma de Buenos Aires (AR); Giselle Ghersi, Ciudad Autonoma de Buenos Aires (AR); Marina Sandra Palermo, Pcia. de Buenos Aires (AR); Maria Pilar Mejias, Pcia. de Buenos Aires (AR); Leticia Veronica Bentancor, Pcia. de Buenos Aires (AR)

(73) Assignees: IMMUNOVA S.A., Ciudad Autónoma de Buenos Aires (AR); CONSEJO NACIONAL DE INVESTIGACIONES CIENTIFICAS Y TECNICAS, Ciudad Autónoma de Buenos Aires (AR)

( * ) Notice: Subject to any disclaimer, the term of this patent is extended or adjusted under 35 U.S.C. 154(b) by 241 days.

(21) Appl. No.: 14/894,484

(22) PCT Filed: May 26, 2014

(86) PCT No.: PCT/IB2014/061731

§ 371 (c)(1),
(2) Date: Nov. 27, 2015

(87) PCT Pub. No.: WO2014/191903

PCT Pub. Date: Dec. 4, 2014

(65) Prior Publication Data

US 2016/0115459 A1 Apr. 28, 2016

Related U.S. Application Data

(60) Provisional application No. 61/827,713, filed on May 27, 2013.

(51) Int. Cl.
*C12N 9/10* (2006.01)
*A61K 39/108* (2006.01)
(Continued)

(52) U.S. Cl.
CPC ............ *C12N 9/1085* (2013.01); *A61K 38/45* (2013.01); *A61K 39/0258* (2013.01); *A61K 39/098* (2013.01); *C07K 14/245* (2013.01); *C07K 16/1232* (2013.01); *C07K 16/18* (2013.01); *C07K 16/40* (2013.01); *A61K 38/00* (2013.01); *A61K 2039/505* (2013.01); *A61K 2039/523* (2013.01); *A61K 2039/545* (2013.01); *A61K 2039/55505* (2013.01); *A61K 2039/55566* (2013.01); *A61K 2039/575* (2013.01); *A61K 2039/6037* (2013.01); *A61K 2039/6068* (2013.01); *C07K 2317/20* (2013.01); *C07K 2317/22* (2013.01); *C07K 2317/31* (2013.01); *C07K 2317/565* (2013.01); *C07K 2317/569* (2013.01); *C07K 2317/76* (2013.01);
(Continued)

(58) Field of Classification Search
None
See application file for complete search history.

(56) References Cited

U.S. PATENT DOCUMENTS

2009/0087435 A1 4/2009 Goldbaum et al.

FOREIGN PATENT DOCUMENTS

CN 102532324 B 2/2014
WO 99/59629 A1 11/1999
(Continued)

OTHER PUBLICATIONS

Berguer et al., "A Polymeric Bacterial Protein Activates Dendritic Cells via TLR4", 2006. J. Immunol176:2366-2372). 2006. *J. Immunol.* 176:2366-2372.
(Continued)

*Primary Examiner* — Patricia Duffy
(74) *Attorney, Agent, or Firm* — Seed Intellectual Property Law Group LLP

(57) ABSTRACT

Chimeric polypeptides useful as immunogens for inducing protective immune responses and neutralizing antibodies against Shiga toxin (Stx) in mammals. More specifically, chimeric polypeptides having a monomer of the homopentameric B subunit of the Shiga 2 toxin fused to the N-terminus of a monomer of *Brucella* lumazine synthase, and to oligomeric protein complexes formed from said chimeric polypeptides. Polynucleotides and vectors encoding said chimeric polypeptides, transgenic cells having said polynucleotides and vectors, pharmaceutical compositions, such as a vaccine, having said chimeric polypeptides and chimeric polynucleotides, antibodies which bind to the chimeric polypeptides, a method for obtaining antibodies which bind specifically to the subunit B of the Shiga 2 toxin and methods of lowering the bacterial load of enterohemorrhagic *Escherichia coli* in mammals, which can be used for prevention of inter alia, hemolytic-ureic syndrome (HUS), are also provided.

25 Claims, 10 Drawing Sheets

Specification includes a Sequence Listing.

(51) Int. Cl.

| | |
|---|---|
| ***C07K 16/12*** | (2006.01) |
| ***C07K 16/18*** | (2006.01) |
| ***A61K 39/02*** | (2006.01) |
| ***A61K 38/45*** | (2006.01) |
| ***C07K 14/245*** | (2006.01) |
| ***C07K 16/40*** | (2006.01) |
| ***A61K 39/00*** | (2006.01) |
| *A61K 38/00* | (2006.01) |

(52) U.S. Cl.
CPC .. *C07K 2319/55* (2013.01); *C12Y 205/01078* (2013.01); *Y02A 50/474* (2018.01)

(56) References Cited

FOREIGN PATENT DOCUMENTS

| | | | |
|---|---|---|---|
| WO | WO 2005/121330 A2 | | 12/2005 |
| WO | WO 2005/121330 A3 | | 12/2005 |
| WO | WO 2007/115148 | * | 10/2007 |
| WO | 2014/191904 A1 | | 12/2014 |

OTHER PUBLICATIONS

Beutin et al., "Spread of a Distinct Stx2-Encoding Phage Prototype among *Escherichia coli* O104:H4 Strains from Outbreaks in Germany, Norway, and Georgia", 2012. *J. Virol.* 86(19):10444-10455.
Bielaszewska et al., "Localization of Intravenously Administered Verocytotoxins (Shiga-Like Toxins) 1 and 2 in Rabbits Immunized with Homologous and Heterologous Toxoids and Toxin Subunits," 1997, *Infect Immun.,* 65(7):2509-2516.
Boerlin et al., "Associations between Virulence Factors of Shiga Toxin-Producing *Escherichia coli* and Disease in Humans," 1999 *J. Clin. Microbiol.* 37 (3): 497-503.
Braden et al., "Divergence in Macromolecular Assembly: X-ray Crystallographic Structure Analysis of Lumazine Synthase from *Brucella abortus*", 2000. *J. Mol. Biol.,* 297:1031-1036.
Cassataro et al., A recombinant subunit vaccine based on the insertion of 27 amino acids from Omp31 to the N-terminus of BLS induced a similar degree of protection against *B. ovis* than Rev.1 vaccination 2007. *Vaccine* 25:4437-4446.
Conrady et al., "Molecular Basis of Differential B-Pentamer Stability of Shiga Toxins 1 and 2", 2010. *PLoS One*, vol. 5, Iss. 12, 9 pgs.
Donohue-Rolfe et al., "Isolation and characterization of functional Shiga toxin subunits and renatured holotoxin", 1989. *Mol. Microbiol.* 3 (9): 1231-1236.
Donohue-Rolfe et al., "Shiga Toxin: Purification, Structure, and Function", 1991. *Rev. Infect. Dis.* 13 Suppl 4:S293-297.
Fischer et al., "A method for soluble overexpression of the α7 nicotinic acetylcholine receptor extracellular domain", 2001. *Proc. Natl. Acad. Sci .USA* 98 (6):3567-3570.
Fraser et al., "Crystal structure of the holotoxin from *Shigella dysenteriae* at 2.5 Å resolution", 1994. *Nat. Struct. Biol.* 1 (1): 59-64.
Fraser et al., "Structure of Shiga Toxin Type 2 (Stx2) from *Escherichia coli* O157:H7", 2004. *J. Biol. Chem.* 279 (26): 27511-27517.
Gao et al., "Immunogenicity of a novel Stx2B—Stx1B fusion protein in a mice model of Enterohemorrhagic *Escherichia coli* O157:H7 infection", 2009. *Vaccine* 27 (14): 2070-6.
Goldbaum et al., "Crystallization and Preliminary X-Ray Diffraction Analysis of the Lumazine Synthase from *Brucella abortus",* 1998. *J. Struct. Biol.,* 123:175-178.
Head et al., "Preparation of VT1 and VT2 Hybrid Toxins from Their Purified Dissociated Subunits", 1991. *Biol. Chem.* 266 (6): 3617-21.
Imai et al., "Production of Secretory Immunoglobulin A against Shiga Toxin-Binding Subunits in Mice by Mucosal Immunization", 2004. *Infect. Immun.* 72 (2):889-895.
Jackson et al., "Nucleotide sequence analysis of the structural genes for Shiga-like toxin I encoded by bacteriophage 933J from *Escherichia coli*", 1987. *Microb. Pathog.* 2 (2): 147-53.
Karmali et al., "Antigenic Heterogeneity of *Escherichia coli* Verotoxins",1986. *Lancet* 1 (8473): 164-165.
Kitova et al., "Stability of the Homopentameric B Subunits of Shiga Toxins 1 and 2 in Solution and the Gas Phase as Revealed by Nanoelectrospray Fourier Transform Ion Cyclotron Resonance Mass Spectrometry". 2005. *J. Am. Soc. Mass. Spectrom.* 16 (12): 1957-1968.
Kitova et al., "Assembly and Stability of the Shiga Toxins Investigated by Electrospray Ionization Mass Spectrometry", 2009. *Biochemistry* 48 (23): 5365-5374.
Kratz et al., "Native display of complete foreign protein domains on the surface of hepatitis B virus capsids", 1999. *Proc. Natl. Acad. Sci. USA* 96 (5):1915-1920.
Laplagne et al., "Engineering of a polymeric bacterial protein as a scaffold for the multiple display of peptides", 2004. *Proteins* 57:820-828.
Ling et al., "Structure of the Shiga-like Toxin I B-Pentamer Complexed with an Analogue of Its Receptor Gb3", 1998. *Biochemistry* 37 (7): 1777-88.
Ling et al., "A mutant Shiga-like toxin IIe bound to its receptor Gb3: structure of a group II Shiga-like toxin with altered binding specificity", 2000.*Structure* 8 (3): 253-64.
Lingwood, "Role of verotoxin receptors in pathogenesis", 1996. Trends Microbiol 4 (4): 147-53.
Louise and Obrig, "Specific Interaction of *Escherichia coli* O157:H7-Derived Shiga-like Toxin II with Human Renal Endothelial Cells", 1995. *J. Infect. Dis.* 172 (5): 1397-401.
Ludwig et al., "Cross-protection against challenge by intravenous *Escherichia coli* verocytotoxin 1 (VT1) in rabbits immunized with VT2 toxoid", 2002. *Can. J. Microbiol.* 48 (1): 99-103.
Marcato et al., "Serum Amyloid P Component Binding to Shiga Toxin 2 Requires Both A Subunit and B Pentamer", *Infect. Immun.* Oct. 2003 vol. 71, No. 10, pp. 6075-6078.
Perera et al., "Identification of Three Amino Acid Residues in the B Subunit of Shiga Toxin and Shiga-Like Toxin Type II That Are Essential for Holotoxin Activity", 1991. *J Bacteriol* 173 (3): 1151-60.
Pina et al., "Thermodynamic Analysis of the Structural Stability of the Shiga Toxin B-Subunit", 2003. *Biochemistry* 42 (31): 9498-9506.
Scotland et al., "Two distinct toxins active on Vero cells from *Escherichia coli* O157", 1985. Lancet 2 (8460): 885-886.
Shimizu et al., "Development of a lethal Shiga toxin-producing *Escherichia coli*-infection mousemodel using multiple mitomycin C treatment", 2003. *Microb. Pathog.* 35 (1):1-9.
Smith et al., "Development of a hybrid Shiga holotoxoid vaccine to elicit heterologous protection against Shiga toxins types 1 and 2", 2006. *Vaccine* 24:4122-4129.
Stein et al., "Crystal structure of the cell-binding B oligomer of verotoxin-1 from *E. coli*", 1992. Nature 355 (6362): 748-750.
Strockbine et al., "Two Toxin-Converting Phages from *Escherichia coil* 0157:H7 Strain 933 Encode Antigenically Distinct Toxins with Similar Biologic Activities", 1986. *Infect. Immun.* 53(1): 135-140.
Tesh et al., "Comparison of the Relative Toxicities of Shiga-Like Toxins Type I and Type II for Mice", 1993. *Infect. Immun.* 61 (8): 3392-3402.
Tsuji et al., "A nasal vaccine comprising B-subunit derivative of Shiga toxin 2 for cross-protection against Shiga toxin types 1 and 2", 2008. *Vaccine* 26 (17): 2092-2099.
Velikovsky et al., "Brucella Lumazine Synthase Elicits a Mixed Th1-Th2 Immune Response and Reduces Infection in Mice Challenged with *Brucella abortus* 544 Independently of the Adjuvant Formulation Used", 2003. *Infect. Immun.*71:5750-5755.
Vogel et al., "Quatemary Structure Is Critical for Protein Display on Capsid-Like Particles (CLPs): Efficient Generation of Hepatitis B Virus CLPs Presenting Monomeric but not Dimeric and Tetrameric Fluorescent Proteins", 2005. *Proteins* 58 (2):478-488.

(56) References Cited

OTHER PUBLICATIONS

Wadolkowski et al., "Acute Renal Tubular Necrosis and Death of Mice Orally Infected with *Escherichia coli* Strains That Produce Shiga-Like Toxin Type II", 1990. *Infect. Immun.* 58 (12): 3959-3965.

Weinstein et al., "In Vivo Formation of Hybrid Toxins Comprising Shiga Toxin and the Shiga-Like Toxins and Role of the B Subunit in Localization and Cytotoxic Activity", 1989. *Infect. Immun.* 57 (12): 3743-3750.

Wen et al., "Genetic toxoids of Shiga toxin types 1 and 2 protect mice against homologous but not heterologous toxin challenge", 2006. *Vaccine* 24 (8): 1142-1148.

Zhang et al., "Subcutaneous and intranasal immunization with Stx2B—Tir—Stx1B—Zot reduces colonization and shedding of *Escherichia coli* O157:H7 in mice", 2011. Vaccine 29 (22): 3923-3929.

Zylberman et al., "High Order Quaternary Arrangement Confers Increased Structural Stability to *Brucella* sp. Lumazine Synthase", 2004. *J. Biol. Chem.,* 279 (9):8093-8101.

Alvarez et al., "Tandem repeats of extracellular domain of Matrix 2 influenza protein exposed in *Brucella* lumazine synthase decameric carrier molecule induce protection in mice". *Vaccine,* 2013 31(5):806-812.

Bellido et al., "*Brucella* spp lumazine synthase as a bovine rotavirus antigen delivery system". 2009. *Vaccine* 27(1):136-145.

Marcato et al., "Immunoprophylactic potential of Cloned Shiga Toxin 2 B Subunit". 2000. *The Journal of Infectious Diseases* 183(3):435-443.

Betancor et al. "A DNA Vaccine Encoding the Enterohemorragic *Escherichia coli* Shiga-Like toxin 2 A2 and B subunits confers Protective Immunity to Shiga Toxin Challenge in the Murine Model". 2009 *Clinical and Vaccine Immunology* 16(5):712-718.

Betancor et al., "Promoter Sequence of Shiga Toxin 2 (Stx2) Is Recognized In Vivo, Leading to Production of Biologically Active Stx2". 2013. *MBIO* 4(5):e00501-13.

Mejias et al., "Immunization with a Chimera Consisting of the B Subunit of Shiga Toxin Type 2 and *Brucella* Lumazine Synthase Confers Total Protection against Shiga Toxins in Mice". 2013. *The Journal of Immunology* 191(5):2403-2411.

Acheson et al., "Expression and Purification of Shiga-Like Toxin II B Subunits," *Infection and Immunity 63*(1):301-308, 1995.

Chichili et al., "Linkers in the structural biology of protein—protein interactions," *Protein Science 22*(2):153-167, 2013.

Kimura et al., "Development of humanized monoclonal antibody TMA-15 which neutralizes Shiga toxin 2," *Hybrid Hybridomics 21*(3):161-168, 2002.

Ma et al., "Engineering an anti-Stx2 antibody to control severe infections of EHEC O157:H7," *Immunol. Lett. 121*(2):110-115, 2008.

Mejias et al., "Protection of Mice against Shiga Toxin 2 (Stx2)-Associated Damage by Maternal Immunization with a Brucella Lumazine Synthase-Stx2 B Subunit Chimera," *Infect. Immun. 82*(4):1491-1499, 2014.

Rocha et al., "Interaction between Shiga Toxin and Monoclonal Antibodies: Binding Characteristics and in Vitro Neutralizing Abilities," *Toxins 4*(9):729-747, 2012.

Sheoran et al., "Human antibody against shiga toxin 2 administered to piglets after the onset of diarrhea due to *Escherichia coli* O157:H7 prevents fatal systemic complications," *Infect. Immun. 73*(8):4607-4613, 2005.

* cited by examiner

```
                        SEQUENCE LISTING

<160> NUMBER OF SEQ ID NOS: 21

<210> SEQ ID NO 1
<211> LENGTH: 70
<212> TYPE: PRT
<213> ORGANISM: Escherichia coli

<400> SEQUENCE: 1

Ala Asp Cys Ala Lys Gly Lys Ile Glu Phe Ser Lys Tyr Asn Glu Asp
1               5                   10                  15

Asp Thr Phe Thr Val Lys Val Asp Gly Lys Glu Tyr Trp Thr Ser Arg
            20                  25                  30

Trp Asn Leu Gln Pro Leu Leu Gln Ser Ala Gln Leu Thr Gly Met Thr
        35                  40                  45

Val Thr Ile Lys Ser Ser Thr Cys Glu Ser Gly Ser Gly Phe Ala Glu
    50                  55                  60

Val Gln Phe Asn Asn Asp
65                  70


<210> SEQ ID NO 2
<211> LENGTH: 174
<212> TYPE: DNA
<213> ORGANISM: Escherichia coli

<400> SEQUENCE: 2

aaaattgagt tttccaagta taatgaggat gacacattta cagtgaaggt tgacgggaaa      60

gaatactgga ccagtcgctg gaatctgcaa ccgttactgc aaagtgctca gttgacagga     120

atgactgtca caatcaaatc cagtacctgt gaatcaggct ccggatttgc tgaa           174


<210> SEQ ID NO 3
<211> LENGTH: 228
<212> TYPE: PRT
<213> ORGANISM: Artificial Sequence
<220> FEATURE:
<223> OTHER INFORMATION: Synthetic construct

<400> SEQUENCE: 3

Met His Ala Asp Cys Ala Lys Gly Lys Ile Glu Phe Ser Lys Tyr Asn
1               5                   10                  15

Glu Asp Asp Thr Phe Thr Val Lys Val Asp Gly Lys Glu Tyr Trp Thr
            20                  25                  30

Ser Arg Trp Asn Leu Gln Pro Leu Leu Gln Ser Ala Gln Leu Thr Gly
        35                  40                  45

Met Thr Val Thr Ile Lys Ser Ser Thr Cys Glu Ser Gly Ser Gly Phe
    50                  55                  60

Ala Glu Val Gln Phe Asn Asn Asp Gly Ser Gly Ser Gly Leu Lys Thr
65                  70                  75                  80

Ser Phe Lys Ile Ala Phe Ile Gln Ala Arg Trp His Ala Asp Ile Val
                85                  90                  95
```

```
Asp Glu Ala Arg Lys Ser Phe Val Ala Glu Leu Ala Ala Lys Thr Gly
            100                 105                 110

Gly Ser Val Glu Val Glu Ile Phe Asp Val Pro Gly Ala Tyr Glu Ile
        115                 120                 125

Pro Leu His Ala Lys Thr Leu Ala Arg Thr Gly Arg Tyr Ala Ala Ile
    130                 135                 140

Val Gly Ala Ala Phe Val Ile Asp Gly Gly Ile Tyr Arg His Asp Phe
145                 150                 155                 160

Val Ala Thr Ala Val Ile Asn Gly Met Met Gln Val Gln Leu Glu Thr
                165                 170                 175

Glu Val Pro Val Leu Ser Val Val Leu Thr Pro His His Phe His Glu
            180                 185                 190

Ser Lys Glu His His Asp Phe Phe His Ala His Phe Lys Val Lys Gly
        195                 200                 205

Val Glu Ala Ala His Ala Ala Leu Gln Ile Val Ser Glu Arg Ser Arg
    210                 215                 220

Ile Ala Leu Val
225


<210> SEQ ID NO 4
<211> LENGTH: 687
<212> TYPE: DNA
<213> ORGANISM: Artificial Sequence
<220> FEATURE:
<223> OTHER INFORMATION: Synthetic construct

<400> SEQUENCE: 4

atgcatgcgg attgtgctaa aggtaaaatt gagttttcca agtataatga ggatgacaca      60

tttacagtga aggttgacgg gaaagaatac tggaccagtc gctggaatct gcaaccgtta     120

ctgcaaagtg ctcagttgac aggaatgact gtcacaatca aatccagtac ctgtgaatca     180

ggctccggat ttgctgaagt gcagtttaat aatgacggtt ctggttctgg tcttaagaca     240

tcctttaaaa tcgcattcat tcaggcccgc tggcacgccg acatcgttga cgaagcgcgc     300

aaaagctttg tcgccgaact ggccgcaaag acgggtggca gcgtcgaggt agagatattc     360

gacgtgccgg gtgcatatga aattcccctt cacgccaaga cattggccag aaccgggcgc     420

tatgcagcca tcgtcggtgc ggccttcgtg atcgacggcg gcatctatcg tcatgatttc     480

gtggcgacgg ccgttatcaa cggcatgatg caggtgcagc ttgaaacgga agtgccggtg     540

ctgagcgtcg tgctgacgcc gcaccatttc catgaaagca aggagcatca cgacttcttc     600

catgctcatt tcaaggtgaa gggcgtggaa gcggcccatg ccgccttgca gatcgtgagc     660

gagcgcagcc gcatcgcgct tgtctga                                         687


<210> SEQ ID NO 5
<211> LENGTH: 233
<212> TYPE: PRT
<213> ORGANISM: Artificial Sequence
<220> FEATURE:
<223> OTHER INFORMATION: Synthetic construct

<400> SEQUENCE: 5

Met His Ala Asp Cys Ala Lys Gly Lys Ile Glu Phe Ser Lys Tyr Asn
1               5                   10                  15

Glu Asp Asp Thr Phe Thr Val Lys Val Asp Gly Lys Glu Tyr Trp Thr
            20                  25                  30

Ser Arg Trp Asn Leu Gln Pro Leu Leu Gln Ser Ala Gln Leu Thr Gly
```

-continued

```
        35                  40                  45

Met Thr Val Thr Ile Lys Ser Ser Thr Cys Glu Ser Gly Ser Gly Phe
    50                  55                  60

Ala Glu Val Gln Phe Asn Asn Asp Gly Ser Gly Ser Gly Ser Gly Ser
65                  70                  75                  80

Gly Ser Leu Lys Thr Ser Phe Lys Ile Ala Phe Ile Gln Ala Arg Trp
                85                  90                  95

His Ala Asp Ile Val Asp Glu Ala Arg Lys Ser Phe Val Ala Glu Leu
            100                 105                 110

Ala Ala Lys Thr Gly Gly Ser Val Glu Val Glu Ile Phe Asp Val Pro
        115                 120                 125

Gly Ala Tyr Glu Ile Pro Leu His Ala Lys Thr Leu Ala Arg Thr Gly
    130                 135                 140

Arg Tyr Ala Ala Ile Val Gly Ala Ala Phe Val Ile Asp Gly Gly Ile
145                 150                 155                 160

Tyr Arg His Asp Phe Val Ala Thr Ala Val Ile Asn Gly Met Met Gln
                165                 170                 175

Val Gln Leu Glu Thr Glu Val Pro Val Leu Ser Val Val Leu Thr Pro
            180                 185                 190

His His Phe His Glu Ser Lys Glu His His Asp Phe Phe His Ala His
        195                 200                 205

Phe Lys Val Lys Gly Val Glu Ala Ala His Ala Ala Leu Gln Ile Val
    210                 215                 220

Ser Glu Arg Ser Arg Ile Ala Leu Val
225                 230


<210> SEQ ID NO 6
<211> LENGTH: 702
<212> TYPE: DNA
<213> ORGANISM: Artificial Sequence
<220> FEATURE:
<223> OTHER INFORMATION: Synthetic construct

<400> SEQUENCE: 6

atgcatgcgg attgtgctaa aggtaaaatt gagttttcca agtataatga ggatgacaca     60

tttacagtga aggttgacgg gaaagaatac tggaccagtc gctggaatct gcaaccgtta    120

ctgcaaagtg ctcagttgac aggaatgact gtcacaatca aatccagtac ctgtgaatca    180

ggctccggat ttgctgaagt gcagtttaat aatgacggtt ctggttctgg ttctggttct    240

ggttctctta agacatcctt taaaatcgca ttcattcagg cccgctggca cgccgacatc    300

gttgacgaag cgcgcaaaag ctttgtcgcc gaactggccg caaagacggg tggcagcgtc    360

gaggtagaga tattcgacgt gccgggtgca tatgaaattc cccttcacgc caagacattg    420

gccagaaccg ggcgctatgc agccatcgtc ggtgcggcct tcgtgatcga cggcggcatc    480

tatcgtcatg atttcgtggc gacggccgtt atcaacggca tgatgcaggt gcagcttgaa    540

acggaagtgc cggtgctgag cgtcgtgctg acgccgcacc atttccatga aagcaaggag    600

catcacgact tcttccatgc tcatttcaag gtgaagggcg tggaagcggc ccatgccgcc    660

ttgcagatcg tgagcgagcg cagccgcatc gcgcttgtct ga                      702


<210> SEQ ID NO 7
<211> LENGTH: 238
<212> TYPE: PRT
<213> ORGANISM: Artificial Sequence
<220> FEATURE:
<223> OTHER INFORMATION: Synthetic construct
```

<400> SEQUENCE: 7

Met His Ala Asp Cys Ala Lys Gly Lys Ile Glu Phe Ser Lys Tyr Asn
1               5                   10                  15

Glu Asp Asp Thr Phe Thr Val Lys Val Asp Gly Lys Glu Tyr Trp Thr
            20                  25                  30

Ser Arg Trp Asn Leu Gln Pro Leu Leu Gln Ser Ala Gln Leu Thr Gly
        35                  40                  45

Met Thr Val Thr Ile Lys Ser Ser Thr Cys Glu Ser Gly Ser Gly Phe
    50                  55                  60

Ala Glu Val Gln Phe Asn Asn Asp Gly Ser Gly Ser Gly Ser Gly Ser
65                  70                  75                  80

Gly Ser Gly Ser Gly Ser Gly Leu Lys Thr Ser Phe Lys Ile Ala Phe
                85                  90                  95

Ile Gln Ala Arg Trp His Ala Asp Ile Val Asp Glu Ala Arg Lys Ser
            100                 105                 110

Phe Val Ala Glu Leu Ala Ala Lys Thr Gly Gly Ser Val Glu Val Glu
        115                 120                 125

Ile Phe Asp Val Pro Gly Ala Tyr Glu Ile Pro Leu His Ala Lys Thr
    130                 135                 140

Leu Ala Arg Thr Gly Arg Tyr Ala Ala Ile Val Gly Ala Ala Phe Val
145                 150                 155                 160

Ile Asp Gly Gly Ile Tyr Arg His Asp Phe Val Ala Thr Ala Val Ile
                165                 170                 175

Asn Gly Met Met Gln Val Gln Leu Glu Thr Glu Val Pro Val Leu Ser
            180                 185                 190

Val Val Leu Thr Pro His His Phe His Glu Ser Lys Glu His His Asp
        195                 200                 205

Phe Phe His Ala His Phe Lys Val Lys Gly Val Glu Ala Ala His Ala
    210                 215                 220

Ala Leu Gln Ile Val Ser Glu Arg Ser Arg Ile Ala Leu Val
225                 230                 235

<210> SEQ ID NO 8
<211> LENGTH: 717
<212> TYPE: DNA
<213> ORGANISM: Artificial Sequence
<220> FEATURE:
<223> OTHER INFORMATION: Synthetic construct

<400> SEQUENCE: 8
atgcatgcgg attgtgctaa aggtaaaatt gagttttcca agtataatga ggatgacaca 60
tttacagtga aggttgacgg gaaagaatac tggaccagtc gctggaatct gcaaccgtta 120
ctgcaaagtg ctcagttgac aggaatgact gtcacaatca aatccagtac ctgtgaatca 180
ggctccggat ttgctgaagt gcagtttaat aatgacggtt ctggttctgg ttctggttct 240
ggttctggtt ctggttctgg tcttaagaca tcctttaaaa tcgcattcat tcaggcccgc 300
tggcacgccg acatcgttga cgaagcgcgc aaaagctttg tcgccgaact ggccgcaaag 360
acgggtggca gcgtcgaggt agagatattc gacgtgccgg gtgcatatga aattcccctt 420
cacgccaaga cattggccag aaccgggcgc tatgcagcca tcgtcggtgc ggccttcgtg 480
atcgacggcg gcatctatcg tcatgatttc gtggcgacgg ccgttatcaa cggcatgatg 540
caggtgcagc ttgaaacgga agtgccggtg ctgagcgtcg tgctgacgcc gcaccatttc 600
catgaaagca aggagcatca cgacttcttc catgctcatt tcaaggtgaa gggcgtggaa 660

-continued gcggcccatg ccgccttgca gatcgtgagc gagcgcagcc gcatcgcgct tgtctga 717

<210> SEQ ID NO 9
<211> LENGTH: 158
<212> TYPE: PRT
<213> ORGANISM: Brucella abortus

<400> SEQUENCE: 9

Ala Ser Asn Gln Ser Cys Pro Asn Lys Thr Ser Phe Lys Ile Ala Phe
1 5 10 15

Ile Gln Ala Arg Trp His Ala Asp Ile Val Asp Glu Ala Arg Lys Ser
20 25 30

Phe Val Ala Glu Leu Ala Ala Lys Thr Gly Gly Ser Val Glu Val Glu
35 40 45

Ile Phe Asp Val Pro Gly Ala Tyr Glu Ile Pro Leu His Ala Lys Thr
50 55 60

Leu Ala Arg Thr Gly Arg Tyr Ala Ala Ile Val Gly Ala Ala Phe Val
65 70 75 80

Ile Asp Gly Gly Ile Tyr Arg His Asp Phe Val Ala Thr Ala Val Ile
85 90 95

Asn Gly Met Met Gln Val Gln Leu Glu Thr Glu Val Pro Val Leu Ser
100 105 110

Val Val Leu Thr Pro His His Phe His Glu Ser Lys Glu His His Asp
115 120 125

Phe Phe His Ala His Phe Lys Val Lys Gly Val Glu Ala Ala His Ala
130 135 140

Ala Leu Gln Ile Val Ser Glu Arg Ser Arg Ile Ala Leu Val
145 150 155

<210> SEQ ID NO 10
<211> LENGTH: 30
<212> TYPE: DNA
<213> ORGANISM: Artificial Sequence
<220> FEATURE:
<223> OTHER INFORMATION: Synthetic primer

<400> SEQUENCE: 10
atcaacatgc atgcggattg tgctaaaggt 30

<210> SEQ ID NO 11
<211> LENGTH: 45
<212> TYPE: DNA
<213> ORGANISM: Artificial Sequence
<220> FEATURE:
<223> OTHER INFORMATION: Synthetic primer

<400> SEQUENCE: 11
taaaatctta agaccagaac cagaaccgtc attattaaac tgcac 45

<210> SEQ ID NO 12
<211> LENGTH: 33
<212> TYPE: DNA
<213> ORGANISM: Artificial Sequence
<220> FEATURE:
<223> OTHER INFORMATION: Synthetic primer

<400> SEQUENCE: 12
gtttaagaat tcgaaggaga taccaccatg cat 33

<210> SEQ ID NO 13

-continued

<211> LENGTH: 37
<212> TYPE: DNA
<213> ORGANISM: Artificial Sequence
<220> FEATURE:
<223> OTHER INFORMATION: Synthetic primer

<400> SEQUENCE: 13
cgtagcgcga acagactcga tcgtactgac cacctgt 37

<210> SEQ ID NO 14
<211> LENGTH: 30
<212> TYPE: DNA
<213> ORGANISM: Artificial Sequence
<220> FEATURE:
<223> OTHER INFORMATION: Synthetic primer

<400> SEQUENCE: 14
atcaacatgc atgcggattg tgctaaaggt 30

<210> SEQ ID NO 15
<211> LENGTH: 60
<212> TYPE: DNA
<213> ORGANISM: Artificial Sequence
<220> FEATURE:
<223> OTHER INFORMATION: Synthetic primer

<400> SEQUENCE: 15
taaaatctta agagaaccag aaccagaacc agaaccagaa ccgtcattat taaactgcac 60

<210> SEQ ID NO 16
<211> LENGTH: 33
<212> TYPE: DNA
<213> ORGANISM: Artificial Sequence
<220> FEATURE:
<223> OTHER INFORMATION: Synthetic primer

<400> SEQUENCE: 16
gtttaagaat tcgaaggaga taccaccatg cat 33

<210> SEQ ID NO 17
<211> LENGTH: 37
<212> TYPE: DNA
<213> ORGANISM: Artificial Sequence
<220> FEATURE:
<223> OTHER INFORMATION: Synthetic primer

<400> SEQUENCE: 17
cgtagcgcga acagactcga tcgtactgac cacctgt 37

<210> SEQ ID NO 18
<211> LENGTH: 30
<212> TYPE: DNA
<213> ORGANISM: Artificial Sequence
<220> FEATURE:
<223> OTHER INFORMATION: Synthetic primer

<400> SEQUENCE: 18
atcaacatgc atgcggattg tgctaaaggt 30

<210> SEQ ID NO 19
<211> LENGTH: 75
<212> TYPE: DNA
<213> ORGANISM: Artificial Sequence
<220> FEATURE:
<223> OTHER INFORMATION: Synthetic primer

<400> SEQUENCE: 19

-continued

```
taaaatctta agaccagaac cagaaccaga accagaacca gaaccagaac cagaaccgtc     60

attattaaac tgcac                                                      75


<210> SEQ ID NO 20
<211> LENGTH: 33
<212> TYPE: DNA
<213> ORGANISM: Artificial Sequence
<220> FEATURE:
<223> OTHER INFORMATION: Synthetic primer

<400> SEQUENCE: 20

gtttaagaat tcgaaggaga taccaccatg cat                                  33


<210> SEQ ID NO 21
<211> LENGTH: 37
<212> TYPE: DNA
<213> ORGANISM: Artificial Sequence
<220> FEATURE:
<223> OTHER INFORMATION: Synthetic primer

<400> SEQUENCE: 21

cgtagcgcga acagactcga tcgtactgac cacctgt                              37
```

CHIMERAS OF *BRUCELLA* LUMAZINE SYNTHASE AND BETA SUBUNIT OF $AB_5$ TOXINS

TECHNICAL FIELD

The present invention relates to chimeric polypeptides useful as immunogens for inducing protective immune responses and neutralizing antibodies against Shiga toxin (Stx) in mammals. More specifically, the present invention relates to chimeric polypeptides comprising a monomer of the homopentameric B subunit of the Shiga 2 toxin fused to the N-terminus of a monomer of *Brucella* lumazine synthase, and to oligomeric protein complexes formed from said chimeric polypeptides. The invention further relates to polynucleotides and vectors encoding said chimeric polypeptides, to transgenic cells comprising said polynucleotides and vectors, and to pharmaceutical compositions, such as a vaccine, comprising said chimeric polypeptides and chimeric polynucleotides. Also within the scope of the invention are antibodies which bind to the chimeric polypeptides of the invention, a method for obtaining antibodies which bind specifically to the subunit B of the Shiga 2 toxin and methods of lowering the bacterial load of enterohemorrhagic *Escherichia coli* in mammals, which can be used for prevention of inter alia, hemolytic-ureic syndrome (HUS).

BACKGROUND ART

Enterohemorrhagic *Escherichia coli* (EHEC) strains are important human food-borne pathogens (Kaper et al., 2004. *Nat Rev Microbiol* 2:123-140). The clinical manifestations of EHEC infections range from watery diarrhea, or hemorrhagic colitis (HC), to the most severe outcome, the life-threatening hemolytic-uremic syndrome (HUS) (Karmali 1989. *Clin Microbiol Rev* 2:15-38). The infection correlates with ingestion of contaminated meat or vegetables, but is also transmitted by water or even person-to-person contact (Caprioli et al., 2005. *Vet Res* 36:289-311; Griffin and Tauxe, 1991. *Epidemiol Rev* 13:60-98). Sporadic or massive outbreaks have been reported in several developed countries. In other countries, such as in Argentina, HUS shows an endemic behavior and represents a serious public health problem with high morbidity and mortality values (Lopez et al., 2000. *Infect Dis Clin North Am* 14:41-65, viii; Rivas et al., 2006. *Medicina* (*B Aires*) 66 Suppl 3:27-32).

A striking feature of EHEC infection is the production of potent Shiga toxins, responsible of HUS development (Noel and Boedeker, 1997. *Dig Dis* 15:67-91; O'brien et al., *Curr Top Microbiol Immunol* 180:65-94). The Shiga toxin family is a group of structurally and functionally related $AB_5$ exotoxins, which includes Shiga toxin (Stx) produced by *Shigella dysenteriae* serotype 1 and the Shiga toxins that are produced by enterohemorrhagic *Escherichia coli* (EHEC) strains. The EHEC can produce two types of Stx, Shiga toxin type 1 (Stx1) and type 2 (Stx2), and their allelic variants. The genes for Shiga toxins are encoded by lysogenic lamboid bacteriophages (Schmidt, 2001. *Res Microbiol* 152 (8): 687-95), and a given bacteria may express more than one Stx, as they may contain more than one Stx-encoding bacteriophage.

All Shiga toxin family members have an $AB_5$ molecular configuration (Stein et al., 1992. *Nature* 355 (6362): 748-50; Fraser et al., 1994. *Nat Struct Biol* 1 (1): 59-64), in which an enzymatically active monomeric A subunit, StxA (which has a molecular mass of 32 kDa) is non-covalently associated with a B subunit, StxB, responsible for binding to cell surface receptors. StxB is a homopentameric protein (a pentamer of identical monomers, each having a molecular mass of 7.7 kDa). StxB forms a ring-like structure with a central pore into which the carboxyl terminus of StxA inserts (Fraser et al., 1994. *Nat Struct Biol* 1 (1): 59-64). StxA and the StxB subunits are secreted into the bacterial periplasm, where they assemble non-covalently into the holotoxin, as was initially described for heat-labile enterotoxins from *E. coli* (Hirst et al., 1984. *Proc Natl Acad Sci USA* 81 (24): 7752-6).

StxA possesses a highly specific RNA N-glycosidase activity that cleaves an adenine base at position 4,324 on the α-sarcin loop located on domain VI of 28S ribosomal RNA (rRNA) of eukaryotic ribosomes, thereby inhibiting elongation factor-dependent aminoacyl tRNA binding and subsequent chain elongation (Endo et al., 1988. *Eur J Biochem* 171 (1-2): 45-50). Bacterial ribosomes are also a substrate for StxA, and exposure to Shiga toxin type 1 (Stx1) results in decreased proliferation of susceptible bacteria (Suh et al., 1998. *Biochemistry* 37 (26): 9394-8).

StxA subunit is composed of two fragments linked by a disulfide bridge, which is proteolytically cleaved by enzymes in the cytosol and endoplasmic reticulum, generating the A1 subunit of 27 kDa responsible for the enzymatic activity and releasing the smaller A2 fragment (Garred et al., 1995. *J Biol Chem* 270 (18): 10817-21). Austin and collaborators showed that while StxA and StxB can form the holotoxin spontaneously in vitro, the recombinant A1 fragment cannot bind to StxB, indicating that the fragment A2 is essential for the assembly of the holotoxin (Austin et al., 1994. *Infect Immun* 62 (5): 1768-75).

While StxA is responsible for the toxic effect, the StxB pentamer is responsible for binding to a specific receptor in eukaryotic cells. StxB binds to the neutral glycosphingolipid globotriaosylceramide (Gb3; also known as Cd77 or the Pk blood group antigen), which is present on the surface of cells (Jacewicz et al., 1986. *J Exp Med* 163 (6): 1391-404; Lindberg et al., 1987. *J Biol Chem* 262 (4): 1779-85; Waddell et al., 1990. *Proc Natl Acad Sci USA* 87 (20): 7898-901), leading to subsequent internalization of the toxin. In the absence of StxA, StxB still adopts a pentameric structure that is functionally equivalent to the holotoxin in its ability to bind the receptor (Donohue-Rolfe et al., 1989. *Mol Microbiol* 3 (9): 1231-6). Each B subunit monomer comprises two three-stranded antiparallel β-sheets and an α-helix. The pentamer forms a ring-like structure with a central pore of about an 11 Å diameter delimited by five α-helices and surrounded by β-sheets from pairs of adjacent monomers, forming six-stranded antiparallel β-sheets (Stein et al., 1992. *Nature* 355 (6362): 748-50).

The resolution of the crystal structure of subunit B of Shiga toxin 1 (Stx1B) complexed with a receptor Gb3 trisaccharide analogue revealed three potential binding sites within each monomer of B subunit (referred to as sites 1, 2 and 3) (Ling et al., 1998. *Biochemistry* 37 (7): 1777-88). Therefore, there are 15 Gb3 binding sites in the StxB pentamer. All 15 of the Gb3-binding sites face in the same direction, distal to the A subunit, thereby identifying the membrane interaction surface within the pentamer. The Gb3-binding sites do not interact with each other either directly or through conformational changes.

Site 1 is located in a groove between adjacent B subunits and is characterized by a hydrophobic interaction between the phenyl ring of Phe-30 and the Galβ of the receptor and by hydrogen bonds involving Asp-17, Thr-21, Glu-28 and Gly-60. Site 2 is located on the opposite side of the phenyl ring of Phe-30 in a crevice defined by Gly-63, Asn-32, Arg-33 and Ala-56. The third binding site involves hydrophobic stacking interactions of Galβ against the indole ring of Trp-34 (located in the α-helices surrounding the central pore of Stx1B) and a hydrophobic interaction between Galα and Trp-34 of the adjacent monomer. In addition, Galα hydrogen bonds to Trp34 and Asn35 as well as Asp18 from an adjacent monomer. From these results it can be concluded that at least sites 1 and 3 require the correct assembly of the pentamer to be functional. Mutational studies with Stx1B demonstrated that sites 1 and 2 mediate high affinity interactions and that Stx1 cytotoxic activity is mediated primarily by Gb3 binding to sites 1 and 2. However, site 3 mediates low affinity interactions (Bast et al., 1999. *Mol Microbiol* 32 (5): 953-60). Although the affinity of site 3 may be too low to significantly contribute to the strength of cell binding, Ling and collaborators proposed that it could serve other purposes. One reason for this belief is the fact that the tryptophan residue at position 34 is conserved despite being fully exposed to the solvent. These authors proposed that site 3 may play a role helping to sequester a greater number of Gb3 molecules in the membrane below the toxin (Ling et al., 2000. *Structure* 8 (3): 253-64). Thus, all three oligosaccharide-binding sites are required for full biological activity.

The study of Stx2B has been hampered due to the difficulty of expressing large quantities of the biologically active form (Acheson et al., 1995. *Infect Immun* 63 (1): 301-8). However, analysis of the crystallographic structure of Stx2 predicted the presence of the corresponding trisaccharide binding sites on its B subunit, but also demonstrated that the conformation at site 2 differs distinctively from that of the Shiga toxin from *Shigella* and Stx1 B subunits (Fraser et al., 2004. *J Biol Chem* 279 (26): 27511-7). However, the residues involved in sugar-binding are either conserved in the Shiga toxin family, or are conservatively substituted (Ling et al., 2000. *Structure* 8 (3): 253-64). One exception is the substitution of Glu16 in site 2 of Stx2B for aspartic acid in Stx1B, where the water-mediated hydrogen bond seen for Glu16 is replaced by a direct interaction for Asp16. This substitution might be responsible in part, for the reduced Gb3 affinity of Shiga toxin 2 and its variants.

Site-directed mutagenesis has shown that the conserved residue Gly60 is essential for the cytotoxicity of Stx1 and Stx2. Substitution of this residue would alter the conformation of the β5-β6 loop, which is involved not only in site 1 but also in site 2 (Perera et al., 1991. *J Bacteriol* 173 (3): 1151-60). Site-directed mutagenesis has also shown that Arg33 plays an important role in the cytotoxicity of Stx1 and Stx2. The results can be explained by the extensive involvement of its side chain in hydrogen bonding to the terminal galactose of Gb3 trisaccharides in site 2 (Ling et al., 2000. *Structure* 8 (3): 253-64).

The prototype of the Shiga toxin family is the Stx produced by *Shigella dysenteriae*, which is almost identical to the Stx1 produced by *E. coli*, differing in a single amino acid in the catalytic subunit (O'Loughlin and Robins-Browne, 2001. *Microbes Infect* 3 (6): 493-507). Both Stx1 and Stx2 have different variants, with Stx2 being the most diverse. The Stx1 family consists of Stx1 and Stx1c while Stx2 contains the variants Stx2c, Stx2c2, Stx2d, $Stx2d_{activable}$, Stx2e and Stx2f. Stx1 and Stx2 only have a 56% identity to the amino acid sequence level (Jackson et al., 1987. *Microb Pathog* 2 (2): 147-53). Stx2 variants are 84-99% homologous to Stx2.

While there are significant similarities between Stx1 and Stx2 in their basic structure, receptor recognition and biochemical mechanisms of action, there are considerable differences in the clinical impact of patients infected with EHEC strains producing Stx1, Stx2 or both. In principle, one would predict that both Stx1 and Stx2 would put the patient at risk of developing HUS. However, numerous epidemiological studies have shown that Stx2-producing strains are more frequently associated with HUS development than Stx1-producing strains or strains that produce both toxins (Scotland et al., 1987. *Epidemiol Infect* 99 (3): 613-24; Ostroff et al., 1989. *J Infect Dis* 160 (6): 994-8; Donohue-Rolfe et al., 2000. *J Infect Dis* 181 (5): 1825-9).

Regarding the differences between Stx1 and Stx2, the most significant of them are the differences in affinities for the Gb3 receptor and ability to induce toxicity. Although Stx1 and Stx2 have the same functional receptor, Stx1 has a 10 fold higher affinity for Gb3 compared to Stx2 (Head et al., 1991. *Biol Chem* 266 (6): 3617-21). A study using the BIAcore system showed that, although the rate of association of Stx1 to Gb3 is greater than Stx2, the dissociation of Stx2 from the receptor is slower than Stx1 indicating that, while Stx2 binds to the receptor slower, it also dissociates at a slower rate (Nakajima et al., 2001. *J Biol Chem* 276 (46): 42915-22).

Despite the higher affinity of Stx1 for Gb3, and consistent with the epidemiological studies, Stx2 has a lethal dose in mice of 50% ($LD_{50}$), 400 times lower than Stx1 (Tesh et al., 1993. *Infect Immun* 61 (8): 3392-402). Similar results were also obtained when human renal microvascular endothelial cells were treated with Stx1 or Stx2, with Stx2 being found to be about 1000-fold more toxic (Louise and Obrig, 1995. *J Infect Dis* 172 (5): 1397-401). Different studies have made it clear that the B subunits are critical determinants of the differential toxicity of Stx1 and Stx2 in vivo. In cell-free in vitro translation inhibition assays, Stx1 and Stx2 A subunit toxicities are indistinguishable, suggesting that the enzymatic activities of these subunits are not responsible for the large in vivo differences between the two toxins. In contrast, animal models comparing wild-type and chimeric Stx toxicity demonstrate that the presence of the Stx2B subunit is a critical determinant of lethality in vitro and in vivo (Weinstein et al., 1989. *Infect Immun* 57 (12): 3743-50; Head et al., 1991. *Biol Chem* 266 (6): 3617-21; Lingwood, 1996. *Trends Microbiol* 4 (4): 147-53; Marcato et al., 2003. *Infect Immun* 71 (10): 6075-8).

Using mass spectrometry techniques, Kitova et al. reported that Stx1B was primarily pentameric at subunit concentrations ranging from 5 to 85 μM, independently of the ionic strength (Kitova et al., 2005. *J Am Soc Mass Spectrom* 16 (12): 1957-68; Kitova et al., 2009. *Biochemistry* 48 (23): 5365-74). These data were supported by circular dichroism (CD) and dynamic scanning calorimetry (DSC) studies of Stx1B showing a highly thermostable pentamer (Pina et al., 2003. *Biochemistry* 42 (31): 9498-506). In contrast, the degree of assembly of Stx2B subunit is strongly dependent on temperature, subunit concentration and ionic strength. At a subunit concentration of more than 50 μM, the Stx2B subunit exists predominantly as a pentamer, although smaller multimers (dimer, trimer and tetramer) are also evident. At lower concentrations, the Stx2B subunit exists predominantly as monomers and dimers. Conrady and collaborators confirmed and quantified the differences observed by Kitova et al. (2005) in a direct solution-state technique. These authors reported that the Stx2B pentamer is approximately 50 times less stable in solution at pH 7.4 than the Stx1B pentamer (Conrady et al., 2010. *PLoS One* 5 (12): e15153).

Another important difference between Stx1 and Stx2 is observed at the immunological level. Although these two types of Stx were initially identified because antibodies directed against one variant did not cross-react against the other, the study of cross-reactivity (and cross-neutralization) between these two toxins has been the subject of controversy over the years. In vitro studies indicate that these two toxins are serologically distinct and that antibodies directed against one toxin are not capable of neutralizing the other (Scotland et al., 1985. *Lancet* 2 (8460): 885-6; Karmali et al., 1986. *Lancet* 1 (8473): 164-5; Strockbine et al., 1986. *Infect Immun* 53 (1): 135-40). Similarly, Wen et al. showed that immunization of mice with genetically inactivated Stx1 or Stx2 toxoids was able to generate anti-toxin serum IgG against homologous but not heterologous toxin and that these antibodies provided specific protective immunity against challenge with only the homologous toxin (Wen et al., 2006. *Vaccine* 24 (8): 1142-8). However, in other studies with animals immunized with toxoid preparations of Stx1 or Stx2, animals showed cross-protection against challenge with either toxin due to the production of antibodies against the A subunit. Bielaszweska et al. found that immunization of rabbits with chemically inactivated Stx1 or Stx2 toxoids, or the A subunits of each toxin, prevented the heterologous toxin localization in target tissues during development of the systemic pathology mediated by the toxin. In that study, the B subunits of Stx1 or Stx2 did not provide heterologous protection (Bielaszewska et al., 1997. *Infect Immun* 65 (7): 2509-16). Further evidence of cross-protection in vivo was reported by Ludwig et al., where protection of rabbits against challenge with Stx1 was obtained by immunization with a chemically inactivated Stx2 toxoid (Ludwig et al., 2002. *Can J Microbiol* 48 (1): 99-103).

Cross-reactivity between B subunits of Stx is also controversial. Some studies have shown that antibodies against the B subunits of Stx1 or Stx2 do not provide cross-protection (Wadolkowski et al., 1990. *Infect Immun* 58 (12): 3959-65; Bielaszewska et al., 1997. *Infect Immun* 65 (7): 2509-16). For this reason, several authors have proposed the use of fusion proteins between Stx2B and Stx1B to provide protection against both toxins (Gao et al., 2009. *Vaccine* 27 (14): 2070-6; Zhang et al., 2011. *Vaccine* 29 (22): 3923-9). However, Tsuji et al. reported that intranasal immunization of mice with the construction Stx2B-HIS (Stx2B with a histidine tag) was able to confer cross-protection against Stx1 but that the opposite was not true (Tsuji et al., 2008. *Vaccine* 26 (17): 2092-9).

Stx2 variants are distinguishable by differences in biological activity, immunological reactivity or receptor specificity. Stx2 and its variants preferentially bind to Gb3 glycosphingolipid, with the exception of Stx2e, which binds preferentially to globotetraosylceramide (Gb4) (Lingwood, 1996. *Trends Microbiol* 4 (4): 147-53). While Stx2 and Stx2c are the most virulent Stx2 variants, and are associated with the majority of cases of HUS (Boerlin et al., 1999. *J Clin Microbiol* 37 (3): 497-503), Stx2e is the only one not associated with hemorrhagic colitis and HUS in humans and is instead responsible for the edema disease in pigs (MacLeod et al., 1991. *Vet Pathol* 28 (1): 66-73). Furthermore, $Stx2d_{activable}$ differs from all other types of Stx in that it can be activated by elastase, a component of intestinal mucus which cleaves the last two residues of the A subunit to release the fragment A2 (Scheiring et al., 2008. *Pediatr Nephrol* 23 (10): 1749-60).

Despite the magnitude of the social and economic problems caused by EHEC infections, no licensed vaccine or effective therapy is presently available for human use. One of the biggest challenges is to develop an effective and safe immunogen to ensure non-toxicity but also a strong input to host immune system to induce long-lasting, high affinity antibodies that ensure a good neutralization capacity in serum. The B subunit of Stx2 (Stx2B) is the most attractive candidate because, among the Stx family, Stx2 is the most pathogenic toxin, and a Stx2B-based immunogen would protect against the Stx most related to HUS development (Smith et al., 2006. *Vaccine* 24:4122-4129; Wen et al., 2006. *Vaccine* 24 (8): 1142-8; Tsuji et al., 2008. *Vaccine* 26 (17): 2092-9). In addition, the B subunit represents the binding unit of the toxin and is non-toxic for mammalian cells (Donohue-Rolfe et al., 1991. *Rev Infect Dis* 13 Suppl 4:S293-297; Lingwood, 1996. *Trends Microbiol* 4 (4): 147-53). Antibodies able to block the binding process to the specific receptor (Gb3) in mammalian cells should prevent the first step of the toxicity cascade (Ling et al., 1998. *Biochemistry* 37 (7): 1777-88). In addition, an Stx-based vaccine against HUS would not only protect against known EHEC strains, typically O157 and non-O157 serotypes, but it would also be useful against new or rare pathogenic strains of Shiga-toxin-producing *E. coli*, as was the case of the recent large outbreak of HUS caused by the 0104:H4 strain (Beutin et al., 2012. *J Virol* 86:10444-10455; Scheutz et al., 2011. *Euro Surveill* 16).

Despite multiple approaches, a successful Stx2B-based immunogen has not been obtained, mainly because Stx2B is a very poor immunogen (Marcato et al., 2001. *J Infect Dis* 183:435-443; Imai et al., 2004. *Infect Immun* 72 (2):889-895). Two of the three binding sites are formed by residues contributed by neighboring monomers, thus requiring the right assembly of the pentamer for the binding sites to be active (Ling et al., 1998. *Biochemistry* 37 (7): 1777-88). As discussed above, the Stx2B pentamer is only marginally stable in the absence of the A subunit, and when used as immunogen, it is unable to raise specific antibodies against conformational epitopes that are located mostly at the interfaces between monomers of the pentamer.

DISCLOSURE OF THE INVENTION

The inventors have surprisingly discovered that a non-pathogenic, stable Stx antigen capable of eliciting an immune response adequate for immunization and/or production of antibodies against Stx can be produced by creating a chimeric peptide which comprises a monomer of the B subunit of the Shiga toxin type 2 (Stx2B) fused to a monomer of *Brucella* lumazine synthase (BLS). Unexpectedly, when such chimeric peptides form an oligomeric complex of five identical monomers, the conformational epitopes in Stx2 subunit B are stabilized, making the highly stable BLS-Stx2B fusion protein a valuable immunogen in the fight against HUS.

Therefore, according to a first aspect, the present invention comprises a chimeric protein comprising a peptide that has at least 95% amino acid sequence identity to the monomer of the B subunit of the Shiga toxin type 2, said peptide being fused directly or through a peptide linker to a monomer of *Brucella* lumazine synthase.

The B subunit of the Shiga toxin type 2 may be fused directly or through a peptide linker to the N-terminus of a monomer of *Brucella* lumazine synthase. By "the N-terminus of a monomer of *Brucella* lumazine synthase is meant any of the ten most amino terminal amino acids, such as the first, second, third, fourth, fifth, sixth, seventh, eighth, ninth or tenth amino acid from the amino terminus.

The monomer of *Brucella* lumazine synthase may have at least 95% sequence identity to SEQ ID No.: 9, such as at least 96%, at least 97%, at least 98%, at least 99% or more sequence identity.

The monomer of *Brucella* lumazine synthase may have one or more replacements, deletions and/or insertions within the first 8 N-terminal amino acid positions so that the combination of deletions and insertions does not result in an elongation of more than 5 amino acids with respect to SEQ ID No.: 9. For example, the monomer of *Brucella* lumazine synthase may have one, two, three, four, five, six, seven, or eight replacements, deletions and/or insertions within the first 8 N-terminal amino acid positions so that the combination of deletions and insertions does not result in an elongation of more than 5 amino acids with respect to SEQ ID No.: 9.

In a preferred embodiment of the invention, the monomer of the subunit B of the Shiga toxin (SEQ ID No: 1) is linked to the N-terminus of the monomer of *Brucella* lumazine synthase by a peptide linker, such as a G/S flexible peptide, which may be a G/S flexible peptide which is between 2 and 20 amino acids long, or between 5 and 15 amino acids long, such as chimeric peptides comprising the amino acid SEQ ID No: 3, SEQ ID No: 5, or SEQ ID No: 7, and preferably SEQ ID No: 5.

According to another aspect, the present invention comprises a protein oligomeric complex characterized in that it comprises a dimer of pentamers of the chimeric protein of the invention.

According to a further aspect, the present invention comprises a polynucleotide encoding for the chimeric protein of the invention, such as a DNA molecule comprising SEQ ID No: 4, SEQ ID No: 6, or SEQ ID No: 8, and preferably SEQ ID No: 6.

According to yet another aspect, the present invention comprises a vector comprising a polynucleotide encoding the chimeric protein of the invention, such as a vector comprising SEQ ID No: 4, SEQ ID No: 6, or SEQ ID No: 8, and preferably SEQ ID No: 6.

The present invention also comprises a transgenic cell which comprises the polynucleotide or vector of the invention. In a particular embodiment, the transgenic cell is an *E. coli* cell, preferably an *E. coli* BL21 (DE3) cell. In another embodiment, the transgenic cell is a mammalian cell, preferably a 293T cell. In yet another embodiment, the transgenic cell is a *Pichia pastoris* cell.

Another aspect of the invention comprises a pharmaceutical composition comprising the protein oligomeric complex, and/or the vector of the invention and a pharmaceutically suitable vehicle. The pharmaceutical composition of the invention is preferably a vaccine. In a preferred embodiment, in the vaccine of the invention the oligomeric complex comprises an amino acid sequence selected from the group consisting of SEQ ID No: 3, SEQ ID No: 5, and SEQ ID No: 7, and preferably SEQ ID No: 5.

A further aspect of the present invention comprises a method of producing the chimeric protein of the invention, said method comprising the steps of a) culturing a transgenic cell of the invention which comprises the polynucleotide or vector of the invention under suitable conditions for the expression of said chimeric protein, and b) recovering said chimeric protein.

In yet another aspect, the invention comprises a method for obtaining an antibody which binds specifically to the subunit B of the Shiga toxin 2, said method characterized in that it comprises the steps of:

a) administering to a mammal the protein oligomeric complex of the invention under an immunization scheme suitable for eliciting neutralizing antibodies against said oligomeric complex,
b) obtaining from said mammal a biological sample containing said neutralizing antibodies and/or cells capable of producing said neutralizing antibodies, and
c) using said biological sample as a source for said antibody.

In a preferred embodiment of the method of the invention for obtaining an antibody, the biological sample obtained in step b) contains B cells, which are used in step c) to produce a hybridoma. In a preferred embodiment, the mammal to which the protein oligomeric complex is administrated is a mouse. In another preferred embodiment, the mammal to which the protein oligomeric complex is administrated is a camelid. Antibodies obtained by the method of this aspect of the invention are also contemplated within the scope of the invention.

In another aspect the invention includes a method of lowering the bacterial load of enterohemorrhagic *Escherichia coli* in an animal, such as cattle, by administering the oligomeric complex of the invention to the animal in which a lowering of the bacterial load is desired.

In another aspect the invention includes a method of lowering the bacterial load of enterohemorrhagic *Escherichia coli* in an animal, such as cattle, by administering an antibody of the invention to the animal in which a lowering of the bacterial load is desired.

According to yet a further aspect, the invention comprises a method of inducing resistance against hemolytic-uremic syndrome (HUS) in a mammalian subject, said method comprising administering to said mammal subject the vaccine of the invention, such as a vaccine comprising an oligomeric complex of the invention comprising an amino acid sequence selected from the group consisting of SEQ ID No: 3, SEQ ID No: 5, SEQ ID No: 7, and preferably SEQ ID No: 5.

According to yet a further aspect, the invention comprises the vaccine of the invention for use in a method of inducing resistance against hemolytic-uremic syndrome (HUS) in a mammalian subject.

According to yet a further aspect, the invention comprises the use of the chimeric protein of the invention in the manufacture of a medicament for inducing resistance against hemolytic-uremic syndrome (HUS) in a mammalian subject.

A further aspect of the present invention relates to antibodies which bind to the chimeric protein of the invention. Such antibodies are preferable specific for the chimeric protein of the invention. In this context, the term "specific" means that the antibody preferentially binds to the chimeric protein of the invention, but does not exclude binding to a lesser degree with other proteins. The use of the antibodies of the invention in the manufacture of a pharmaceutical composition for preventing or treating hemolytic-uremic syndrome in a mammal, such as a human, is also part of the invention.

A further aspect of the present invention relates to pharmaceutical compositions comprising the antibodies of the invention and a pharmaceutically suitable carrier. The antibodies and pharmaceutical compositions of the invention are useful for example in a method for treating or preventing hemolytic-uremic syndrome (HUS) in a subject in need thereof, which is yet another aspect of the invention. Such method is preferably used for treating or preventing hemolytic-uremic syndrome (HUS) in a human subject,

L15 (panel C). The structure of these proteins was modeled as described in Example 1. BLS monomers are colored in black whereas the Stx2B monomers fused to the structure of BLS are colored in light grey. The linkers (GSGSG) between Stx2B and BLS is colored in dark grey. The figure was constructed with the program Pymol Molecular Graphics Systems.

Figure 2:
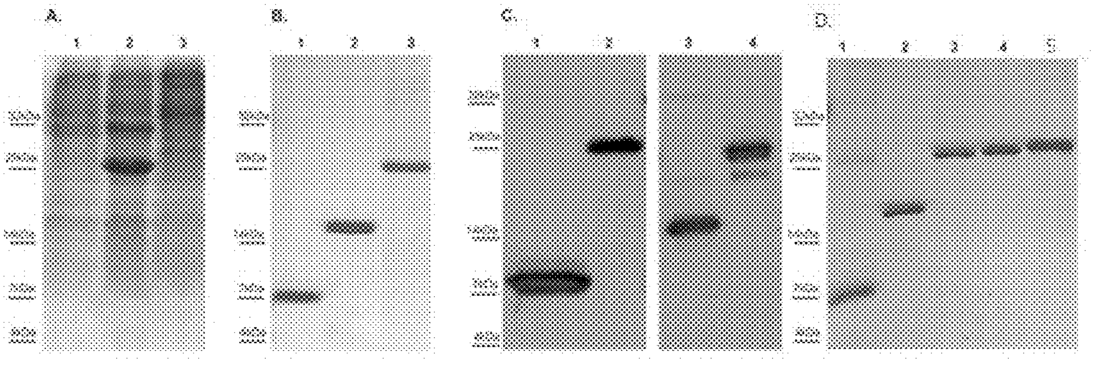

FIG. 2. SDS-PAGE and Western blot analysis of the recombinants Stx2B-BLS. Expressed and purified Stx2-BLS (L10) was separated by 15% SDS-PAGE and stained with Coomassie Blue (A and B), or revealed with specific antibodies (C). The same protocol was performed to all the three chimeras. A) Lane 1, Total proteins of un-induced pET-Stx2B-BLS transformed *E. coli* BL21 (DE3); Lane 2, insoluble pellets of induced pET-Stx2B-BLS transformed *E. coli* BL21 (DE3); Lane 3, soluble fraction of induced pET-Stx2B-BLS transformed *E. coli* BL21 (DE3); B) Lane 1, purified Stx2B; Lane 2: purified BLS; Lane 3: purified Stx2B-BLS. C) Western blot analysis of purified Stx2B-BLS. SDS-PAGE was probed with polyclonal anti-Stx2 mouse IgG (Lanes 1 and 2), or polyclonal anti-BLS mouse IgG (Lanes 3 and 4) and revealed with peroxidase-conjugated rabbit anti-mouse IgG. Lane 1: purified Stx2B; Lane 2: purified Stx2B-BLS; Lane 3: Purified BLS; Lane 4: purified Stx2B-BLS. D) SDS-Page of the purified proteins. Lane 1, Purified Stx2B; Lane 2, Purified BLS; Lane 3, purified Stx2B-BLS L5; Lane 4 purified Stx2B-BLS L10; Lane 5 purified Stx2B-BLS L15.

Figure 3:
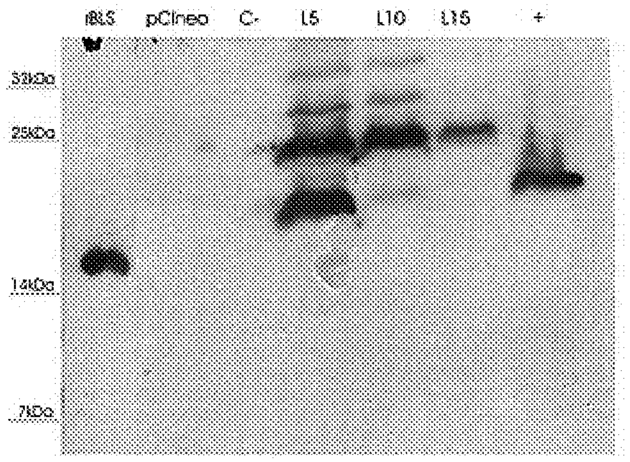

FIG. 3. Western blot analysis of the transfected 293T cells with the plasmid pCineo-BLS-Stx2B-L5, pCineo-BLS-Stx2B-L10 and pCineo-BLS-Stx2B-L15. Lane 1, purified BLS; Lane 2, transfected cells with the pCIneo plasmid empty; Lane 3, negative control of the transfection assay; Lane 4 transfected cells with BLS-Stx2B-L5; Lane 5 transfected cells with BLS-Stx2B L10; Lane 6 transfected cells with BLS-Stx2B-L15.

Figure 4:
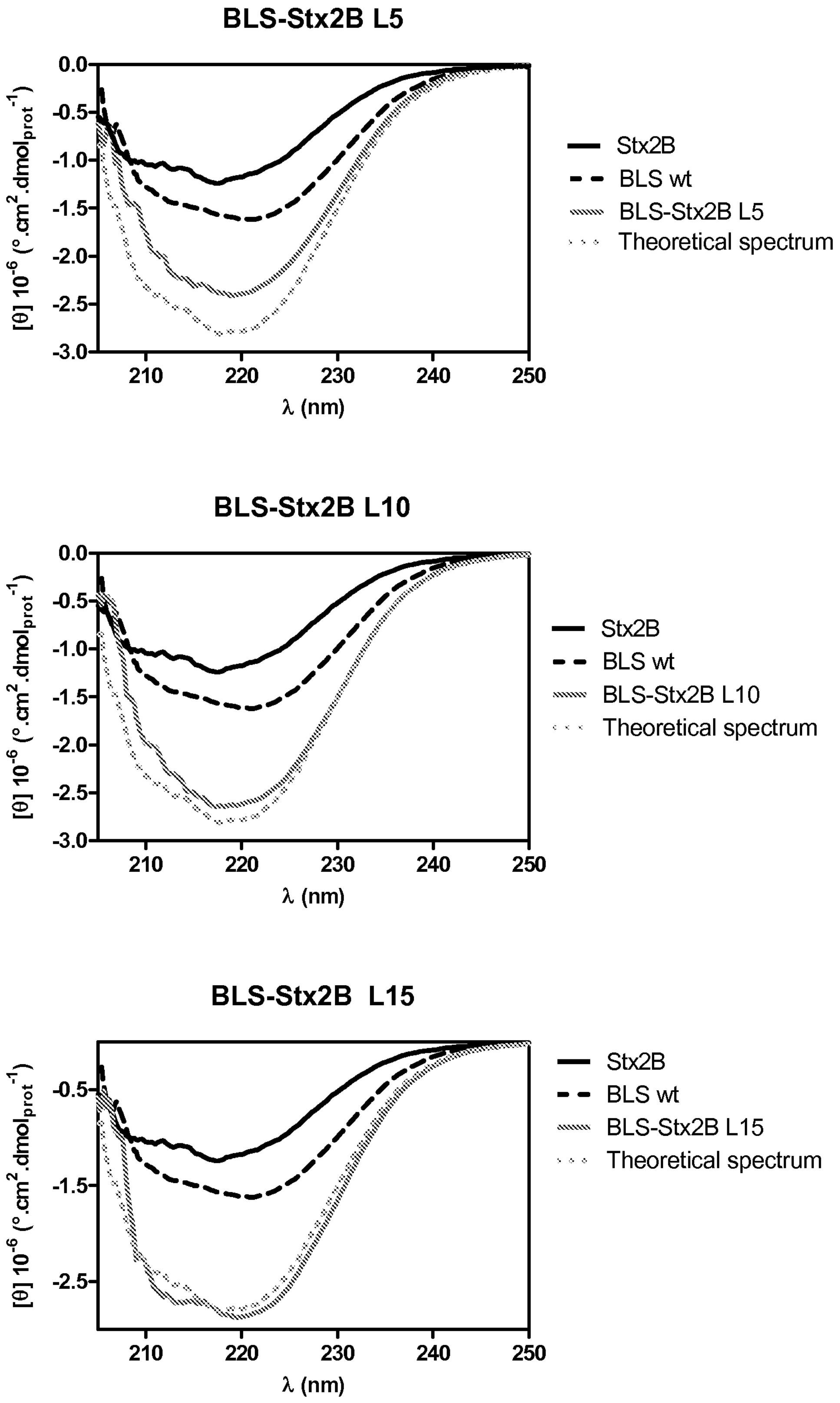

FIG. 4. Comparison of the three far UV-CD spectra of BLSwt (black dashed line), Stx2B (black continuous line) and BLS-Stx2B (grey continuous line). The theoretical spectrum of each BLS-Stx2B chimera, calculated from the combination of the Stx2B and BLS spectra, is represented by a grey dotted line.

Figure 5:
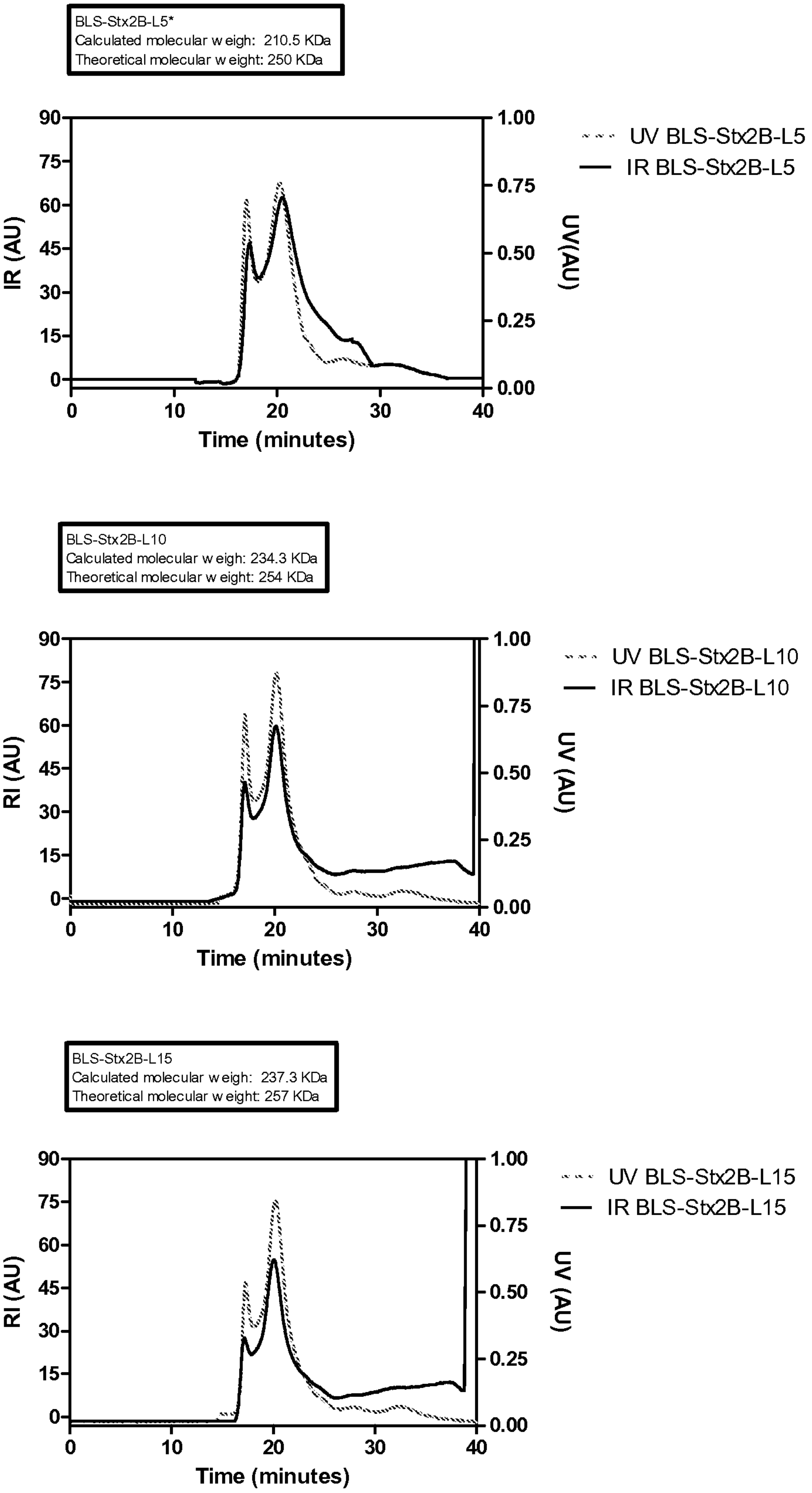

FIG. 5. Size exclusion chromatography (analytical S200 column) coupled to SLS analysis of the three BLS-Stx2B chimeras. All separations were performed at a flow rate of 0.5 mL/min. The elution was monitored by refractive index (continuous line) and UV280 nm (dotted line) signals. The molecular weight of each sample was calculated relating its 90° and RI signals, and comparing of this value with that obtained for BSA as a standard. The first peak corresponds to high MW aggregates, the majority one corresponds to the chimera BLS-Stx2B.

Figure 6:
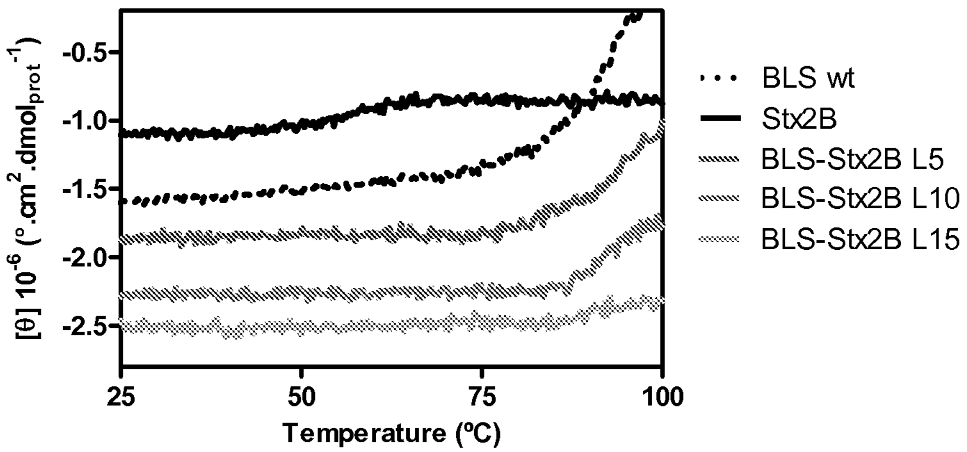

FIG. 6. Thermal denaturation of BLS followed by the 222 nm CD signal of proteins as a function of temperature. Wild type (black dashed line), Stx2B (black continuous line) BLS-Stx2B L5 (dark grey continuous line), BLS-Stx2B L10 (grey continuous line) and BLS-Stx2B L15 (light grey continuous line).

Figure 7:
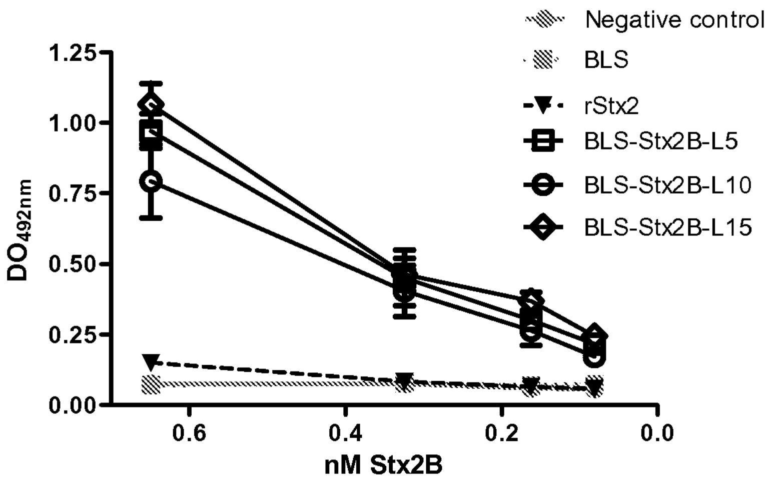

FIG. 7. Assessment of BLS-Stx2B assembly y the Gb3-binding ELISA assay. Serially diluted BLS-Stx2B-L5, BLS-Stx2B-L10, BLS-Stx2B-L15, BLS, rStx2 or *E. coli* BL21 lysate (used as negative control for nonspecific binding) were added to Gb3 coated plates. Binding was determined as detailed in Example 13.

Figure 8:
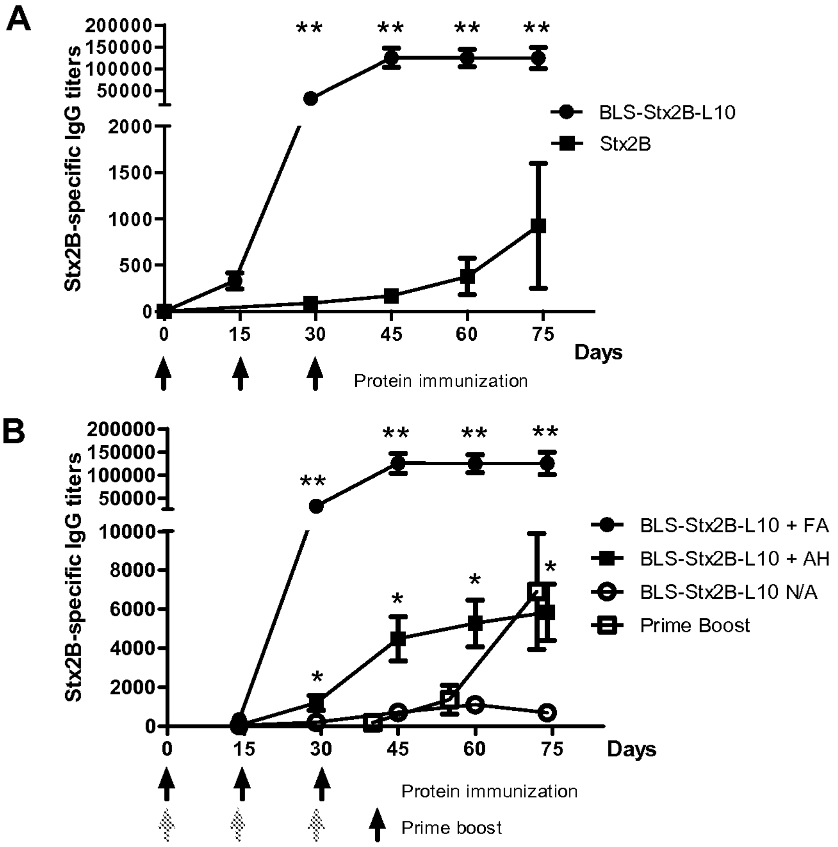

FIG. 8. Time course of specific IgG titers against Stx2B.A) Stx2B-specific IgG titers in sera from mice immunized with BLS-Stx2B-L10 or Stx2B, both formulated in FA, were determined by ELISA. Each time point represents the mean±SEM of 4-6 mice/group. ** P<0.005 vs. the same time point of Stx2B group. B) Stx2B-specific IgG titers in sera from mice immunized with Stx2-BLS-L10 in different formulations or regimens. Each time point represents the mean±SEM of 4-6 mice/group. * P<0.05 vs. the same time point of BLS-Stx2B-L10 with non-adjuvant (N/A) group; ** P<0.005 vs. the same time point of all others groups. Black arrow-heads indicate protein immunizations; Grey arrow-heads indicate DNA immunizations.

Figure 9:
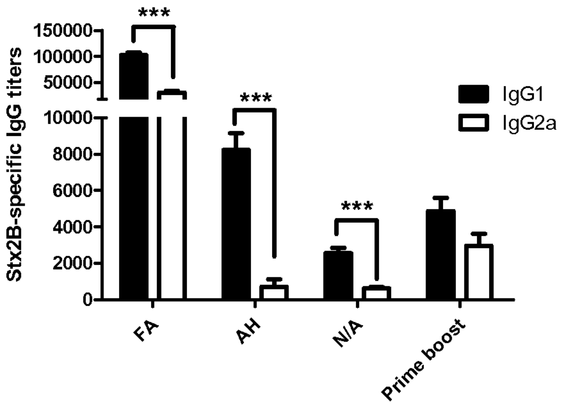

FIG. 9. Subtypes of Stx2B-specific IgG. Sera from mice immunized with different formulations of BLS-Stx2B-L10 were assayed by ELISA as detailed in Materials and Methods. Each bar represents the mean±SEM of 4-6 by group; *** P<0.001 vs. IgG2a in each group.

Figure 10:
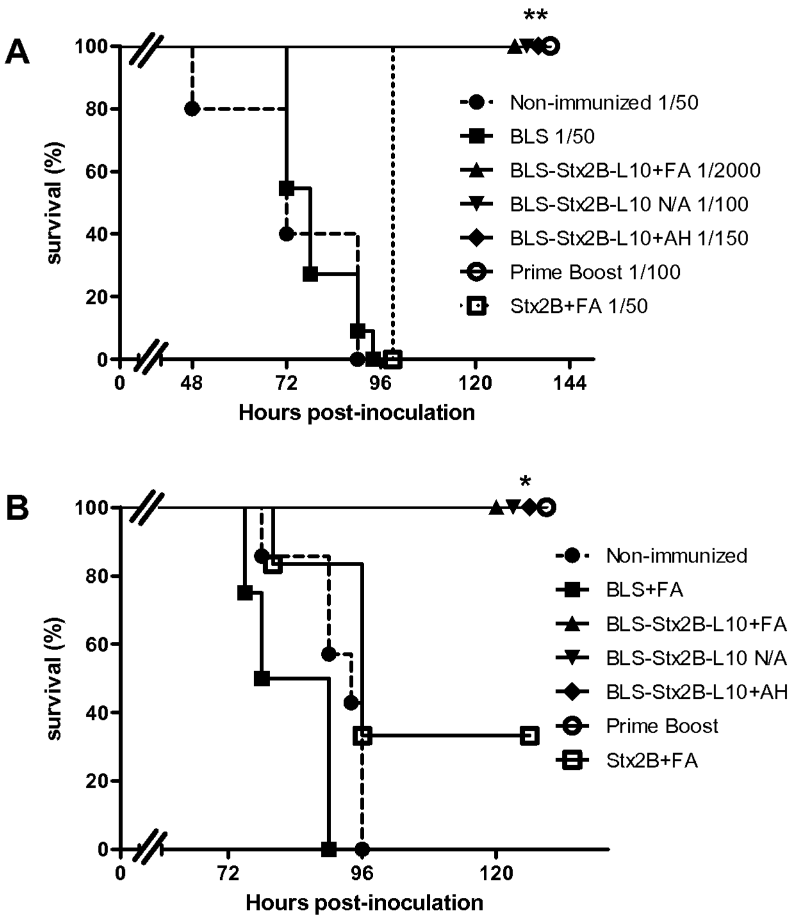

FIG. 10. Mortality curves. A) Ex vivo neutralization of rStx2 toxicity ($1LD_{100}$) with sera from immunized mice Pool of sera from each immunized group (4-6 mice/pool) (45 days post last immunization) or non-immunized mice, was diluted according to the in vitro neutralization titer as indicated in the figure's reference. B) Protection of immunized mice against a lethal challenge of purified rStx2. Adult male BALB/c mice immunized with Stx2B+FA or different formulations of BLS-Stx2B; or BLS+FA (4-6 mice/group) were i.v. challenged with 1 LD100 rStx2 45 days after the last immunization. * P<0.05 vs. Stx2B+FA immunized mice and p<0.005 vs. non-immunized or BLS+FA immunized mice. ** p<0.005 vs. all other groups.

Figure 11:
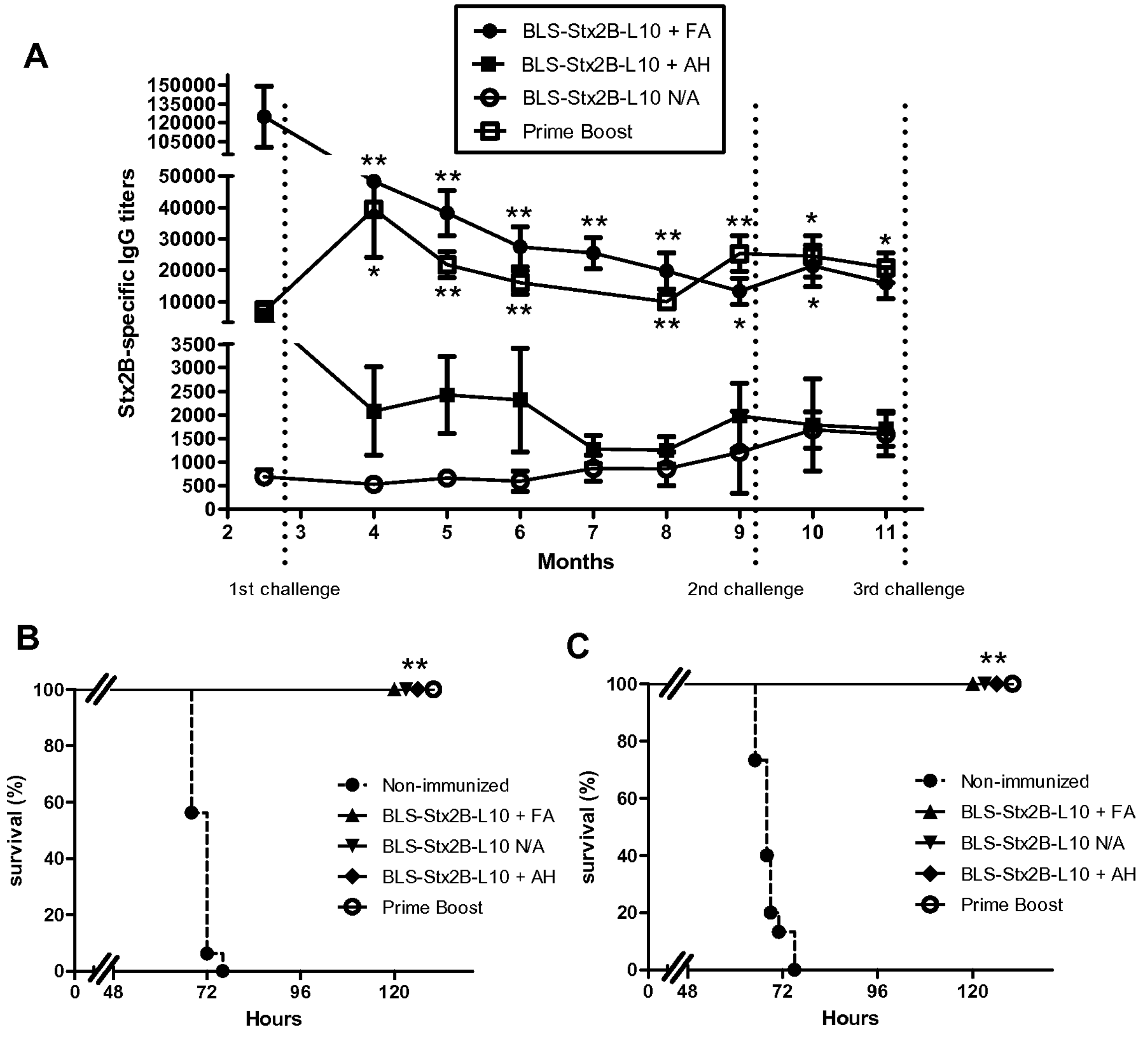

FIG. 11. Long term specific IgG antibody response and protective immune response. A) Titers of specific IgG against Stx2B assayed by ELISA up to 9 months after the last immunization dose; B) Mice surviving the first rStx-challenge received a second challenge with 2LD100 rStx2 at the time indicated in part A ($2^{nd}$ challenge).  P<0.005 compared to BLS-Stx2B-L10 with non-adjuvant (N/A) or AH immunized mice. C) Mice surviving the two first rStx2-challenges, received a third challenge with 3LD100 of rStx2 at the time indicated in part A (3nd challenge).  P<0.005 compared to non-immunized mice FIG. 12: Time course of specific IgG titers with one dose of BLS-Stx2B-L10. Stx2B-specific IgG titers in sera from mice immunized with one dose of BLS-Stx2B-L10 formulated in AH were determined by ELISA. Each time point represents the mean±SEM of 6 mice. Grey arrows indicate challenges with rStx2.

Figure 12:
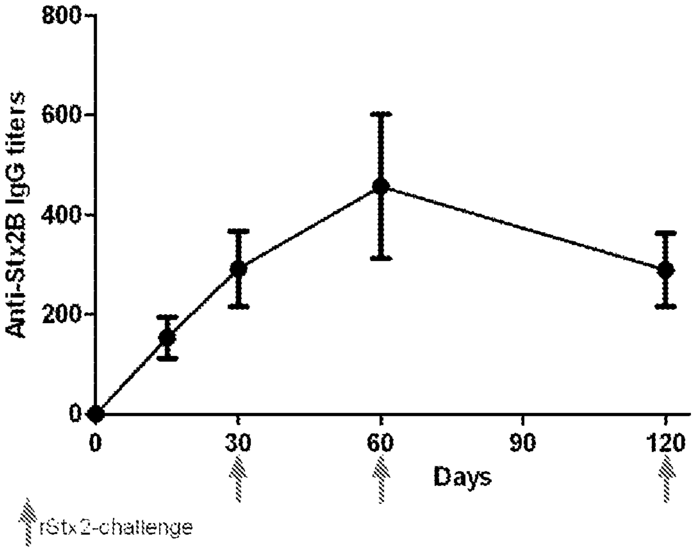
Figure 13:
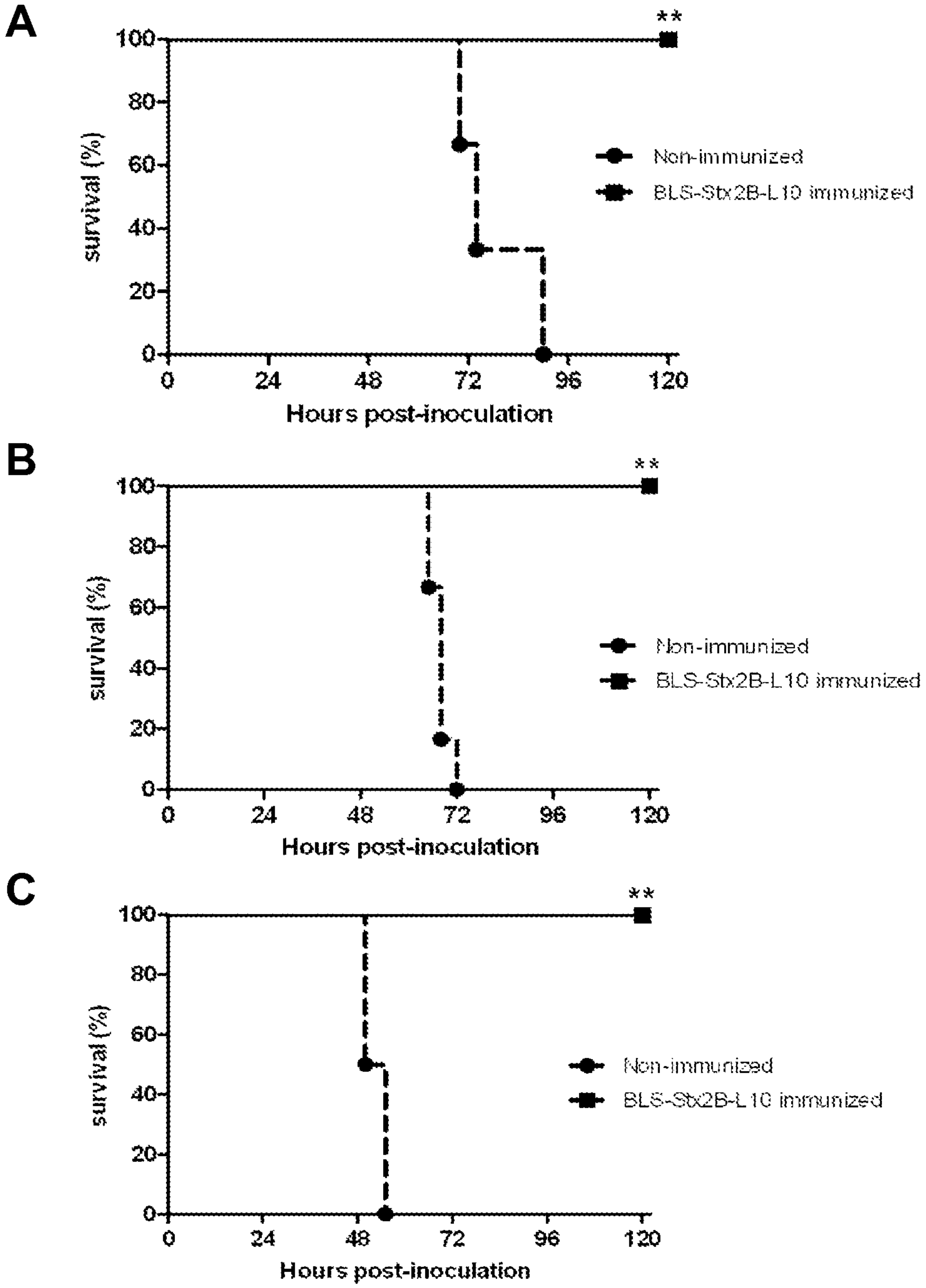

FIG. 13: Mortality curves. Protection of immunized mice against lethal challenges of purified rStx2. Non-immunized or BLS-Stx2B-L10-immunized (one dose) adult BALB/c mice (4-6 mice/group) were i.v. challenged with (A): 1 LD100 rStx2 30 days post-immunization, (B): 3 LD100 rStx2 60 days post-immunization and (C): 5 LD100 rStx2 120 days post-immunization. The different challenges are indicated in grey arrows in FIG. 12. ** P<0.005 vs non-immunized mice.

DETAILED DESCRIPTION OF THE INVENTION

The present invention proposes a novel strategy to overcome the lack of a successful Stx2B-based immunogen: the display of the StxB2 pentamer onto the BLS protein particle. BLS (*Brucella* lumazine synthase) has been described as a very efficient carrier for antigen delivery (Laplagne et al., 2004. *Proteins* 57:820-828; Cassataro et al., 2007. *Vaccine* 25:4437-4446; Bellido et al., 2009. *Vaccine* 27:136-145). BLS is a highly immunogenic and stable dimer of pentamers and a scaffold that has been used to display foreign antigens on its structure (Velikovsky et al., 2003. *Infect Immun* 71:5750-5755; Zylberman et al., 2004. *J Biol Chem* 279: 8093-8101; Bellido et al., 2009. *Vaccine* 27:136-145; Cassataro et al., 2007. *Vaccine* 25:4437-4446; Laplagne et al., 2004. *Proteins* 57:820-828). However, a vast array of difficulties can be envisaged for the use of a protein polymeric scaffold for the display of another polymeric protein: a) the polymerization of the inserted antigen can occur between different protein particles, producing a crossing over and a massive aggregation; b) the kinetics of folding and association of the pentamers of the B subunit and BLS could be very different, thus the folding of the fusion particle could be trapped in an intermediate state; c) the structural constrains imposed for the covalent link to the pentamers of BLS could not be adequate to stabilize the pentameric structure of the B subunit; d) the topology of the oligomeric scaffold may not be compatible with that of the oligomeric target; e) interactions between intermediate configurations of the different proteins could prevent the proper folding and assembly of the fusion particles; f) low stability or low solubility of the fusion target could adversely affect the stability of the whole particle inducing aggregation of the complex.

The display of whole proteins on oligomeric scaffolds can be restrained by an unsuitable structure of the foreign protein and by its propensity to undergo homomeric interactions. The propensity of a candidate insert to undergo homomeric interactions is critical. The display of non-monomeric proteins in the context of oligomeric scaffolds may be problematic because of inter-particle cross-linking and aggregation through homomeric interactions of the target subunits. This phenomenon may be even worse when protomers remain free because of uneven stoichiometry between the target oligomer and BLS.

There are examples where the use of a protein polymeric scaffold known to function correctly for the display of a monomeric protein has resulted in a failure to correctly display another polymeric protein. For instance, Hepatitis B virus-like particles (VLPs) formed by the HBcAg, have been successfully used for the display of monomeric eGFP (Kratz et al., 1999. *Proc Natl Acad Sci USA* 96 (5):1915-1920). However, dimerizing and tetramerizing color variants of GFP, failed to form VLPs (Vogel et al., 2005. *Proteins* 58 (2):478-488). In this case, the key role of insert quaternary structure was demonstrated by successful VLP formation when engineered monomeric variants were used instead. Another example were the attempts to soluble express and improve the folding and assembly of the homopentameric extracellular N-terminal domain (ECD) of the nicotinic acetylcholine receptors (nAChR) by recombinant fusion to homopentameric proteins like cholera toxin B-subunit, icosahedral lumazine synthase from bacteria (formed by 12 assembled pentamers), and lumazine synthase from yeast, all of which have failed (Fischer et al., 2001. *Proc Natl Acad Sci USA* 98 (6):3567-3570). The failure of this approach might be attributed to the folding/association behavior of the fused proteins.

Against all expectations, attachment of the Stx2B subunits to the BLS scaffold promotes the correct pentamerization of the toxin and dramatically stabilizes its structure, in particular its thermodynamic stability, as demonstrated by a large increase in the melting temperature (Tm) from 60 to almost 90° C., thus overcoming the aforementioned lack of stability of the B subunit of the Stx2 toxin when it is not associated with the A subunit. Moreover, the resulting chimera (BLS-Stx2B) shows a remarkable capacity to induce long lasting humoral immune responses, and is able to induce antibodies with high neutralizing capacity for Stx2 and its variants, to the point that mice immunized with BLS-Stx2B are completely protected against high lethal doses of Stx challenge i.p. up to ten months after the last immunization dose. The ability to induce highly specific antibodies indicates that the BLS-Stx2B chimera both preserves the native configuration of the conformational epitopes of Stx2B that constitute the binding sites to Gb3 and allows for their efficient display to the solvent.

The maintenance of the native configuration in the chimera is particularly surprising considering that the BLS scaffold lacks a central projection equivalent to the carboxyl terminus of StxA, which in the holotoxin fills the central pore of the StxB ring-like structure. Thus, in BLS-Stx2B the central pore of Stx2B is unoccupied. Those skilled in the art would expect this to cause at least some change in the geometry and/or symmetry of the Stx2B pentamer, and in turn negatively affect its binding sites, particularly sites 1 and 3 which require the correct assembly of the pentamer to be functional. The BLS scaffold, however, seems to be able to stabilize the Stx2B pentamer without disrupting its Gb3 binding sites.

As discussed under the "Technical Field" section, Stx2 (SEQ ID No: 1) is the most pathogenic Shiga toxin, and an Stx2B-based immunogen would protect against the Stx variants found in most cases of HUS development (Smith et al., 2006. *Vaccine* 24:4122-4129; Wen et al., 2006. *Vaccine* 24 (8): 1142-8; Shimizu et al., 2008. *Microb Pathog* 35 (1):1-9). More significantly, the antibodies induced by the chimera show similar neutralizing capacity to the wild-type Stx2 and its variants, presenting even cross-neutralizing capacity (e.g. antibodies induced by a BLS-Stx2B chimera are able to neutralize Stx1). It has been previously demonstrated that all Gb3 binding sites in this family of toxins are located on the same face of the B pentamer, opposite to the A subunit. Thus, the sera capacity to neutralize different Stx family members would be mainly due to antibodies recognizing these binding sites, which are conserved in all members of the Stx family. This fact is of great importance for prophylaxis or therapeutics of HUS, because antibodies showing broad reactivity against Gb3 binding sites should be highly effective at preventing the damage caused by most of the toxins of the Stx family, making this invention promissory for its use in future outbreaks caused by pathogenic strains of Shiga toxin-producing *E. coli*. Without attaching to any particular explanation, the inventors believe that the strong B cell response elicited when mice are immunized for instance with BLS-Stx2B could be explained by the thermodynamic stabilization of the Stx2B pentamer and also by the ability of BLS to target and activate dendritic cells (Berguer et al., 2006. *J Immunol* 176:2366-2372). Specific ELISA titers and neutralization activity of the antibodies elicited by BLS-Stx2B are significantly improved when compared to those elicited by Stx2B.

According to a first aspect, the present invention comprises a chimeric protein comprising a monomer of the B subunit of the Shiga toxin 2 (Stx2B) fused to a monomer of *Brucella* lumazine synthase (BLS).

The B subunit of the Shiga toxin type 2 may be fused directly or through a peptide linker to the N-terminus of a monomer of *Brucella* lumazine synthase. By "the N-terminus of a monomer of *Brucella* lumazine synthase is meant any of the ten most amino terminal amino acids, such as the first, second, third, fourth, fifth, sixth, seventh, eighth, ninth or tenth amino acid from the amino terminus.

The lumazine synthase enzyme catalyzes the penultimate step in the riboflavin biosynthetic route (see Goldbaum et al., 1999. *J. Med. Microbiol.,* 48:833-839). Its active site is located in the interface among monomers, conferring a very stable polymeric order to this protein (See Ritsert et al., 1995. *J. Mol. Biol.,* 253:151-167).

The lumazine synthase of *Brucella* spp. (BLS) is a highly stable protein. Analyses of immunochemical enzymatic function and tridimensional structure as determined by X-ray crystallography show similar results for the native protein and for the protein expressed recombinantly (see Braden et al., 2000. *J. Mol. Biol.,* 297:1031-1036; Goldbaum et al., 1999. *J. Med. Microbiol.,* 48:833-839; Goldbaum et al., 1998. *J. Struct. Biol.,* 123:175-178). The structure shows that this 18-kDa protein behaves as a 180-kDa decamer in solution, becoming a new type of quaternary arrangement of the lumazine synthase (see Zylberman et al., 2004. *J. Biol. Chem.,* 279 (9):8093-8101). The structure analysis also shows that the N-termini of the monomers of BLS are displayed at the vertices of a symmetric pentamer at a distance of 40 Ångströms between each other, and that the amino terminal 10 amino acids are involved neither in the general folding nor in the contacts among monomers. (see Braden et al., 2000. *J. Mol. Biol.,* 297:1031-1036). This means that some or all of at least the last 8 N-terminal amino acid residues of BLS can be removed or mutated without significantly affecting its usefulness as antigen carrier. Accordingly, in the chimeric peptide of the invention, the BLS moiety can comprise the complete BLS wild sequence or present substitutions, insertions or deletions in one, several or all of the amino acids in the first 8 positions of its N-terminus. Nevertheless, since a number of insertions resulting in an excessive elongation at the N-terminus could have negative effects, such as a decreased solubility and/or ability to elicit an immune response, in the chimeric protein of the invention the combination of deletions and insertions at the N-terminus of the BLS monomer preferably should not result in an elongation of more than 5 amino acids respect to SEQ ID No.: 9. In a preferred embodiment of the invention, the first 8 amino acids at the N-terminus of the lumazine synthase of *Brucella* spp. are deleted.

It is well known that some variation in the amino acid sequence of peptides is possible while maintaining all or part of the biological properties and activity of the original peptide. It is also known that the chances of diminishing or losing the biological activity increase with the degree of departure from the original sequence. Accordingly, chimeric peptides in which the BLS monomer presents some variation respect to the wild BLS sequence are also part of the present invention, in particular those in which the BLS monomer has at least 95% (e.g. 96%, 97%, 98%, 99% or more) sequence identity to SEQ ID No: 9 (without considering the first 8 amino acid positions, as discussed above). Similarly, chimeric peptides in which the Subunit B of the Shiga toxin type II is at least 95% % (e.g. 96%, 97%, 98%, 99% or more) amino acid sequence identity by sequence to the Subunit B of wild Shiga toxin type II are also within the scope of the present invention.

Fusion of the Subunit B of the Shiga toxin type 2 monomer to the BLS monomer can be accomplished in the present invention directly (i.e. by establishing a peptidic union between the C-terminus of the Subunit B monomer and the N-terminus of the BLS monomer), or through a peptide linker. The peptide linker is preferably a G/S peptide, and may be between 2 and 20 amino acids long, or between 5 and 15 amino acids long, including 5, 10 or 15 amino acids long, such as chimeric peptides comprising the amino acid SEQ ID No: 3, SEQ ID No: 5, or SEQ ID No: 7, and preferably SEQ ID No: 5.

When recombinantly expressed, the chimeric proteins of the invention tend to adopt the configuration typical of BLS, that is, a dimer of pentamers. In this oligomeric complex, the five BLS moieties of each pentamer face the five BLS monomers of the other pentamer, and the five Stx moieties of each pentamer are exposed at opposite ends of the decamer. The five Stx monomers on each pentamer preserve thus the molecular configuration of native Stx, and as a result the trisaccharide binding sites of the native B subunit are preserved. In conjunction with its increased stability, the preservation of the conformational epitopes of the Stx B subunit in the BLS-Stx decamer makes them particularly useful as elicitors of an effective and safe immune response. Thus, according to another of its aspects, the present invention comprises a protein oligomeric complex comprising or consisting of two pentamers of the chimeric protein of the invention. Such a protein oligomeric complex is useful both as an immunogen for immunizing a mammal, such as a human, against HUS, and for obtaining anti-Stx antibodies and derivates thereof useful in the treatment of HUS.

The artificial polynucleotides encoding for the chimeric protein of the invention, useful for producing the chimeric protein of the invention and also able to induce cellular or humoral responses when administered to an animal, are also part of the invention. Such polynucleotides are for example, but without being limited to, RNA, genomic DNA or cDNA. In a preferred embodiment, the polynucleotide encoding for the chimeric protein of the invention comprises is a DNA molecule comprising SEQ ID No: 4, SEQ ID No: 6, or SEQ ID No: 8, and more preferably SEQ ID No: 6. The polynucleotides encoding for the chimeric protein of the invention are useful for instance in the construction of vectors such as, but without being limited to, bacterial or viral vectors. Said vectors are able to express, or facilitate the expression of the chimeric proteins of the present invention, and constitute another aspect of the present invention. Vectors comprising polynucleotides encoding for the chimeric protein of the invention can be produced by standard techniques well-known to those skilled in the art. As an example, such vectors can be produced by inserting the polynucleotides encoding for the chimeric protein of the invention in apCi-neo (Promega, USA). In preferred embodiments of the invention, the vectors comprise a polynucleotide encoding for the chimeric protein of the invention of SEQ ID No: 4, SEQ ID No: 6, or SEQ ID No: 8, and more preferably SEQ ID No: 6.

In one embodiment of the invention, the vector comprising the polynucleotide encoding for the chimeric protein of the invention is used to produce a transgenic cell which expresses the chimeric protein of the invention. Such transgenic cells constitute another aspect of the present invention. Cells that can be transformed in the context of the present invention include, but are not limited to, insect cells, bacteria, such as *Escherichia coli*, yeasts such as *Pichia pastoris*, and mammalian cells, such as CHO, COS, BHK, Namalwa and HeLa. In a preferred embodiment of the invention, the transgenic cells are *Escherichia coli* cells, preferably *E. coli* BL21 (DE3). The transgenic cells may also be mammalian cells, such as 293T cells or *Pichia pastoris* cells.

According to another aspect of the present invention, a pharmaceutical composition comprising the protein oligomeric complex of the invention and/or the vector comprising the polynucleotide encoding for the chimeric protein of the invention is provided. The active agents of the pharmaceutical compounds or vaccines of this invention are present in effective physiological doses.

In a preferred embodiment, the pharmaceutical composition of the invention is a vaccine wherein the oligomeric complex comprises an amino acid sequence selected from the group consisting of SEQ ID No: 3, SEQ ID No: 5, and SEQ ID No: 7, and preferably SEQ ID No: 5. The vaccine of the invention is, according to another embodiment of the invention, a DNA vaccine comprising a vector comprising the polynucleotide encoding for the chimeric protein of the invention.

The pharmaceutical composition of the invention is preferably a vaccine useful in inducing resistance against hemolytic-uremic syndrome (HUS) in a mammal subject, and/or in the production of anti-Stx antibodies. Preferably, the pharmaceutical composition of the present invention further comprises a pharmaceutically acceptable carrier. Pharmaceutically acceptable carriers are well-known to the skilled in the art, and its precise nature depends on the kind of formulation and its intended route of delivery, and include solvents and diluents such as water, saline, dextrose, ethanol, glycerol and the like, dispersants, coatings, stabilizing agents such as albumin and EDTA alkali salts, preserving agents, antibacterial and antifungal agents, isotonic agents, etc. In the case of solid formulations, as those intended for its oral administrations, carriers include manitol, lactose, starch, magnesium stearate, sodium saccharine, talc, cellulose, glucose, sucrose, magnesium carbonate and the like.

The vaccine compositions of the present invention include both therapeutic vaccines, administered after the initial infection or after disease outbreak and intended to ameliorate or cure the disease, as well as prophylactic vaccines, administered before the infection and intended to prevent it. The vaccine compositions of the present invention can be prepared by standard methods well-known to the skilled in the art. Preferably, the vaccine compositions of the invention include a pharmaceutically acceptable carrier, as described above. The vaccine compositions contain preferably an adjuvant. Examples of adjuvants are, but without being limited to, oil-water emulsions, such as Freund's adjuvant, aluminum compounds, liposomes, non-ionic block polymers, saponines, and dimethyl dioctadecylamonium bromide (DDA). The vaccine compositions of the present invention can be administered by any of the usual routes, including but not being limited to oral, nasal and injectable (such as intramuscular, intravenous, subcutaneous, intradermal, etc.) route.

The pharmaceutical formulations, such as vaccines, of the present invention can be in a liquid state or in any other pharmaceutical form known in the art, such as injectable emulsions. The pharmaceutical compounds or vaccines described in the present invention can also be in tablets, liquid solutions, suspensions or elixirs for oral administration or in sterile liquids such as solutions or suspensions. Preferably an inert medium is used, such as saline media, phosphate-saline buffers and any other medium where the chimeric proteins, nucleotide sequences or segments thereof have a proper solubility.

The pharmaceutical compositions containing the protein oligomeric complex of the invention and/or the vector comprising the polynucleotide encoding for the chimeric protein of the invention are useful in a method of inducing resistance against hemolytic-uremic syndrome (HUS) in a mammalian subject, which is also part of the invention. In said method, said composition is administered to said mammalian subject. The dose, immunization schedule and need for booster doses will depend on the mammalian species, sanitary condition, age and size of the subject, among other factors, and can be easily determined by those skilled in the art.

A method for producing the chimeric protein comprising a monomer of the B subunit of the Shiga toxin type 2 fused to the N-terminus of a monomer of *Brucella* lumazine synthase (BLS) is also within the scope of this invention. Said method comprises the steps of a) culturing a transgenic cell comprising a polynucleotide encoding for the chimeric protein of the invention under suitable conditions for the expression of said chimeric protein; and b) recovering said chimeric protein. As explained above, when recombinantly expressed, the chimeric protein of the invention adopts the configuration typical of BLS, that is, a dimer of pentamers, thus self-assembling into the oligomeric complex of the invention. The transgenic cell used in this method can be any of the transgenic cells of the invention, including but not being limited to *E. coli* cells, such as *E. coli* BL21 (DE3), *Pichia pastoris* cells, and mammalian cells, such as 293T cells. The protein expressed by the transformed cells can then be recovered and purified by methods known to the skilled in the art, such as by chromatographic methods.

Thanks to its increased stability as compared to the non-chimeric version of Subunit B of Stx2, the protein oligomeric complex of the invention is particularly useful as immunogen for obtaining antibodies which bind specifically to the subunit B of the Shiga toxin, which in turn have medical and diagnostic applications that are readily obvious to the skilled in the art. Thus, the ability of the oligomeric complex of the invention for eliciting an immune response allows its use in a method for producing antibodies which bind specifically to Subunit B of the Shiga toxin, such method being also within the scope of the present invention. Such method comprises the steps of a) administering to a mammal the protein oligomeric complex of the invention under an immunization scheme suitable for eliciting neutralizing antibodies against said chimeric protein; b) obtaining from said mammal a biological sample containing said neutralizing antibodies and/or cells capable of producing said neutralizing antibodies; and c) using said biological sample as a source for said antibody. The biological sample can be of different kinds, and its precise nature will depend upon the particular method by which the antibody of the invention is obtained in step c). For instance, the biological sample can be blood, from where serum containing a polyclonal antibody can be obtained. According to a preferred embodiment of the invention, the biological sample of step b) comprises or consist of B cells, which are used in step c) to produce an antibody-producing hybridoma. The hybridoma technology is well-known to the skilled in the art and has become a standard practice in the field of antibodies. For instance, splenocytes from a mouse immunized against BLS-Stx2B can be fused with myeloma cells to obtain a monoclonal antibody producing hybridoma. In a more preferred embodiment of the invention, the mammal immunized in step a) is a camelid, such as a lama, and the biological sample is blood which contains lymphocyte. From these lymphocytes gene segments encoding specific VHH domains are obtained and used to recombinantly produce VHH fragments which bind specifically to the Subunit B of the Shiga toxin. Due to its small size and increased solubility and stability, VHH fragments (also called single-domain antibodies and nanobodies elsewhere) are easier to formulate and administrate, and can be used to target epitopes usually not reached by conventional antibodies.

The antibodies and antigen-binding fragments thereof obtained through the method of the invention bind specifically to the Subunit B of Shiga toxin, are raised against the conformational epitopes of the chimeric protein of the invention, and are able to efficiently neutralize the Shiga toxin in vivo. These antibodies can be of different sources depending on the animal that is immunized with the chimeric protein of the invention. The antibodies are preferably mouse, human or camelid antibodies or antibody-binding fragments thereof. The antibodies can be polyclonal antibodies or antibody-binding fragments thereof. However, the antibodies obtained through the method of the invention are preferably monoclonal antibodies or recombinant antibodies or antibody-binding fragments thereof, such as mouse monoclonal antibodies or lama antibodies or antibody-binding fragments thereof, preferably single-domain lama antibodies or an antibody-binding fragment thereof, and more preferably a $V_{HH}$. The polynucleotide sequence of the nucleic acids encoding for the antibodies raised by the method of the present invention is easily derived from the sequence of the antibody or $V_{HH}$ in question by the skilled in the art. Said nucleic acids can be used to construct transformation vectors and then be introduced in a host cell by means of standard procedures well known in the art, such as those described in Sambrook et al. (*Molecular Cloning: A Laboratory Manual*, Cold Spring Harbor Laboratory Press, New York, N.Y., 1989).

Also within the scope of this invention is a method for lowering the bacterial load of enterohemorrhagic *Escherichia coli* in cattle. Cattle and other ruminants are primary reservoirs for Shiga toxin-producing *Escherichia coli* (STEC) serotypes that are typically associated with human HUS, e.g., O157:H7. Calves become infected with STEC early in life via horizontal or vertical transmission (Shaw, D. J., C. Jenkins, M. C. Pearce, T. Cheasty, G. J. Gunn, G. Dougan, H. R. Smith, M. E. Woolhouse, and G. Frankel. 2004. Shedding patterns of verocytotoxin-producing *Escherichia coli* strains in a cohort of calves and their dams on a Scottish beef farm. Appl. Environ. Microbiol. 70:7456-7465) and do not develop clinical signs of infection but may shed the bacteria for several months and in great quantities (Widiasih, D. A., N. Ido, K. Omoe, S. Sugii, and K. Shinagawa. 2004. Duration and magnitude of faecal shedding of Shiga toxin-producing *Escherichia coli* from naturally infected cattle. Epidemiol. Infect. 132:67-75).

Reduction of persistent STEC shedding in cattle would contribute greatly to preventing human STEC infections. Evidence that bovine vaccination may be a sensible control option has come from studies in which cattle shed *E. coli* O157 less frequently following immunization with STEC O157:H7 antigens (Potter, A. A., S. Klashinsky, Y. Li, E. Frey, H. Townsend, D. Rogan, G. Erickson, S. Hinkley, T. Klopfenstein, R. A. Moxley, D. R. Smith, and B. B. Finlay. 2004. Decreased shedding of *Escherichia coli* O157:H7 by cattle following vaccination with type III secreted proteins. Vaccine 22:362-369). Cumulating evidence shows that Shiga toxins suppress immune response to STEC antigens during infections. Stx alters the cytokine expression pattern in mucosal macrophages (Stamm, I., M. Mohr, P. S. Bridger, E. Schropfer, M. Konig, W. C. Stoffregen, E. A. Dean-Nystrom, G. Baljer, and C. Menge. 2008. Epithelial and mesenchymal cells in the bovine colonic mucosa differ in their responsiveness to *Escherichia coli* Shiga toxin 1. Infect. Immun. 76:5381-5391) and intraepithelial lymphocytes (Menge, C., M. Blessenohl, T. Eisenberg, I. Stamm, and G. Baljer. 2004. Bovine ileal intraepithelial lymphocytes represent target cells for Shiga toxin 1 from *Escherichia coli*. Infect. Immun. 72:1896-1905) and suppresses the activation and proliferation of mucosal and peripheral lymphocytes in vitro (Moussay, E., I. Stamm, A. Taubert, G. Baljer, and C. Menge. 2006. *Escherichia coli* Shiga toxin 1 enhances IL-4 transcripts in bovine ileal intraepithelial lymphocytes. Vet. Immunol. Immunopathol. 113:367-382). Also, development of an adaptive cellular immune response is significantly delayed following experimental infection of calves with Stx2-producing STEC O157:H7 compared to that in animals inoculated with Stx-negative *E. coli* O157:H7 (Hoffman, M. A., C. Menge, T. A. Casey, W. Laegreid, B. T. Bosworth, and E. A. Dean-Nystrom. 2006. Bovine immune response to Shiga-toxigenic *Escherichia coli* O157:H7. Clin. Vaccine Immunol. 13:1322-1327).

Thus, although is still unknown how O157:H7 *E. coli*-specific cellular immune responses affect long-term and intermittent STEC shedding (Cray, W. C., Jr., and H. W. Moon. 1995. Experimental infection of calves and adult cattle with *Escherichia coli* O157:H7. Appl. Environ. Microbiol. 61: 1586-1590), it has been suggested that inclusion of Stx as an antigen in anti-STEC formulations for bovine vaccines would be beneficial, because it is the only virulence factor shared by all STEC strains, and because Stx-neutralization could improve overall anti-STEC immune response (Fröhlich J1, Baljer G, Menge C. Maternally and naturally acquired antibodies to Shiga toxins in a cohort of calves shedding Shiga-toxigenic *Escherichia coli*. Appl Environ Microbiol. 2009 June; 75(11):3695-704).

Moreover, studies performed in mouse models demonstrated that anti-Stx antibodies are able to inhibit EHEC colonization (Mohawk K L, Melton-Celsa A R, Robinson C M, O'Brien A D. Neutralizing antibodies to Shiga toxin type 2 (Stx2) reduce colonization of mice by Stx2-expressing *Escherichia coli* O157:H7. Vaccine 2010, 28:4777-4785). Among the different mechanisms proposed, it has been shown that Stx2 may contribute positively to EHEC adherence by enhancing the surface expression of nucleolin, which serves as a eukaryotic receptor for intimin (Sinclair J F, O'Brien A D. Cell surface-localized nucleolin is a eukaryotic receptor for the adhesin intimin-gamma of enterohemorrhagic *Escherichia coli* O157:H7. J Biol Chem 2002, 277:2876-2885; Robinson C M, Sinclair J F, Smith M J, O'Brien A D. Shiga toxin of enterohemorrhagic *Escherichia coli* type O157:H7 promotes intestinal colonization. Proc Natl Acad Sci USA 2006, 103:9667-9672).

In the method for lowering the bacterial load of enterohemorrhagic *Escherichia coli* of the invention in mammals such as cattle, the oligomeric complex of the invention is administered to the animal in which a lowering of the bacterial load is desired, thus eliciting an effective immune response against the B subunit of Shiga toxin 2. In turn, this prevents suppression by Shiga toxins of the immune response against STEC antigens, resulting in a reduction of persistent STEC shedding in cattle.

In an alternative method for lowering the bacterial load of enterohemorrhagic *Escherichia coli* of the invention in mammals such as cattle, the antibody of the invention is administered to the animal in which a lowering of the bacterial load is desired.

A further aspect of the present invention relates to antibodies which bind to the chimeric protein of the invention. Such antibodies are preferable specific for the chimeric protein of the invention. In this context, the term "specific" means that the antibody preferentially binds to the chimeric protein of the invention, but does not exclude binding to a lesser degree with other proteins.

The use of the antibodies of the invention in the manufacture of a pharmaceutical composition for preventing or treating hemolytic-uremic syndrome in a mammal, such as a human, is also part of the invention. In that case, the antibodies of the invention are combined with pharmaceutically acceptable carriers for its administration to the mammal in need of prevention or treatment of HUS. Pharmaceutical carriers and pharmaceutical presentations have already been discussed above and are well-known to the expert person.

A further aspect of the present invention relates to pharmaceutical compositions comprising the antibodies of the invention and a pharmaceutically suitable carrier. The antibodies and pharmaceutical compositions of the invention are useful for example in a method for treating or preventing hemolytic-uremic syndrome (HUS) in a subject in need thereof, which is yet another aspect of the invention. Such method is preferably used for treating or preventing hemolytic-uremic syndrome (HUS) in a human subject, such as a human subject infected by a enterohemorrhagic strain of *Escherichia coli.*

EXAMPLE 1

Molecular Modeling of the Chimeric Protein BLS-Stx2

Figure 1:
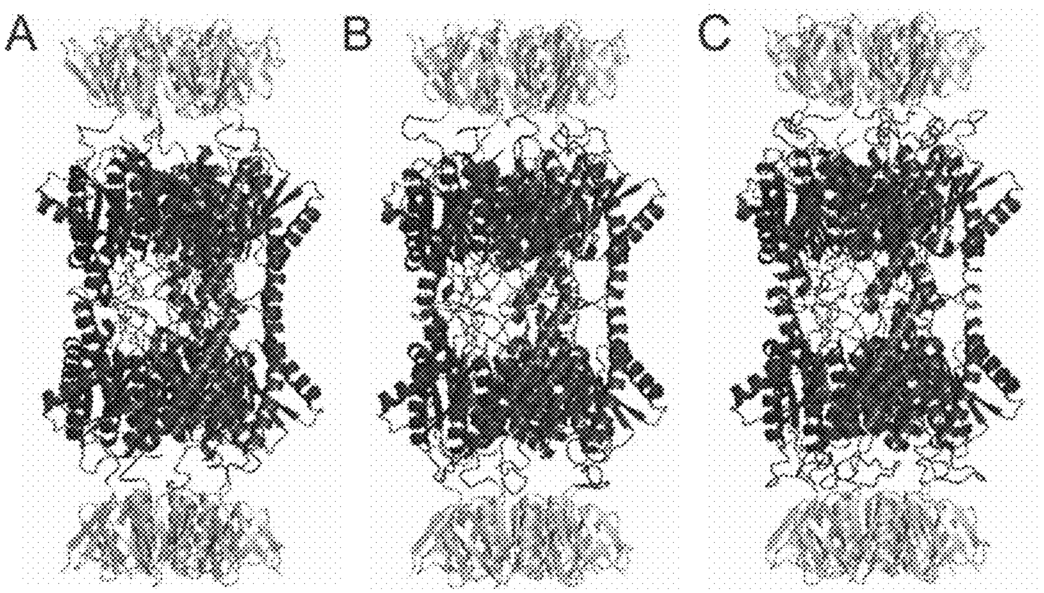
FIG. 1. Theoretical structure of BLS-Stx2B-L5 (panel A) and BLS-Stx2B-L10 chimera (panel B) and BLS-Stx2B-

The design of the chimera was carried out by modeling its theoretical structure with the program PyMOL 1.5 (www.pymol.org) fusing the C-terminal end of the structure of Stx2B (PDB code: IR4P) with the N-terminal end of the crystallographic structure of BLS (PDB code: IDI0), a strategy similar to that described previously by Laplagne et al. (Laplagne et al., 2004. *Proteins* 57:820-828). The coding sequence of the first eight residues of the N-terminal end of BLS was replaced with the coding sequence of Stx2B and a flexible G/S, pentapeptide, decapeptide or a fifteen amino acid peptide linker that connect both proteins. Both Stx2B and BLS form pentameric structures of the same C5 symmetry in which each protomer interacts with other two. The theoretical structure of the chimeras obtained by molecular modeling (FIG. 1) indicates that all the linkers used are long enough to allow the assembly of the Stx2B pentamers onto the pentameric modules of BLS without any steric hindrance. In the decameric BLS particle, two Stx2B pentamers would be displayed in opposite directions at the top and bottom of the structure. It worth noting that in this model the C-terminal surface of Stx2B, which interacts with the A subunit in the Stx2 holotoxin, would be facing the BLS scaffold and maybe protected from interaction with the immune system, whereas the globotriaosylceramide (Gb3) binding sites would be totally exposed.

EXAMPLE 2

The pET11a-BLS-Stx2B-L5 (with the 5 amino acids linker) plasmid containing a gene with the Seq. ID.No.4, was constructed through the following protocol:

a) To clone the codifying gene for the lumazine synthase of *Brucella* spp. (BLS), the BLS sequence was obtained by PCR amplification with specific primers from the genomic DNA of *B. abortus* and cloned in the pET11a vector (Novagen, USA). In order to develop the cassette, a directed mutagenesis was performed over the sequence codifying for the open reading frame of the lumazine synthase of *Brucella* spp. (BLS) (Laplagne et. al 2004). Two new restriction sites were inserted in the 5' region of the BLS gene: an NsiI site in the first two codons of the 5' end, and one AflII site in the two codons comprising the 8 and 9 residues of the native amino acids sequence of BLS.

b) To insert the sequence codifying to the Stx2B protein (Seq. ID. No.1), we designed oligonucleotides that amplify the Stx2B protein with the site of the NsiI enzyme (underlined) at the 5' of the sequence and the site of AflII enzyme (underlined) at the 3' of the sequence plus a sequence that codify for a linker of five amino acids (bold). The Stx2B gene (Seq. ID. No.2) was obtained by PCR from a previously cloned sequence in pGEM-T vector as template (Capozzo et al., 2003. *Infect Immun* 71:3971-3978).

Hence, the following oligonucleotides were built to be used as primers in the PCR:

Primer forward (Seq. ID. NO. 10):

5' ATCAACATGCATGCGGATTGTGCTAAAGGT 3'

Primer reverse 5 (Seq. ID. NO. 11):

5' TAAAATCTTAAGACCAGAACCAGAACCGTCATTATTAAACTGCAC 3'

PCR reaction was carried out with 0.2 mM deoxyribonucleotide triphosphates (dNTPs) (Promega Inc.), 1.5 mM $MgCl_2$ (PBL®), 0.15 Units of DNA Taq Polymerase (PBL®) and 0.5 μM primers. The cycling profile was: 1 cycle of 94° C. for 2 minutes, 35 cycles of 92° C. for 10 seconds, 62° C. for 12 seconds and 72° C. for 30 seconds and 1 final cycle of 72° C. for 2 minutes.

The PCR product was checked using agarose gels and then purified using the Qiagen extraction Kit (Qiagen, UK)

c) The pET11a-BLS plasmid and the purified PCR Stx2B-L5 product were digested with the NsiI and AflII restriction enzymes. Digestion was performed with 3 Units of NsiI (Fermentas Inc.) and 3 Units of AflII (Fermentas Inc) in buffer Tango™ 2× (final concentration) for 4 hours at 37° C. Digested products were ligated with 5 Units of DNA T4 ligase enzyme (Fermentas Inc.) overnight at 16° C. Ligation was transformed in *E. coli* DH5α competent cells and colonies were screened by PCR with specific primers (Forward and Reverse 5). The insertion was confirmed by sequencing. The sequencing analysis showed that the first 8 amino acids of the lumazine synthase of the *Brucella* spp. were replaced by the 70 amino acids from the Stx2B protein (Seq. ID. No.1). Thus, a gene was obtained, which codes for a chimeric fusion protein called BLS-Stx2B (L5) with the Seq. ID. No.3.

EXAMPLE 3

The pCI-Neo-BLS-Stx2B-L5 plasmid, was constructed through the following protocol:

The sequence of the gene of BLS-Stx2B (L5) Seq. ID. No. 4 cloned in pET11a vector was subcloned in the vector pCi-neo (Promega, USA). Hence, the following oligonucleotides were built to be used as primers in the PCR:ACCATG BLS-DNA-chimera all (Seq. ID. No. 12):

5' GTTTAAGAATTCGAAGGAGATACCACCATGCAT 3'

BLS-Back (Seq. ID. No. 13):

3' CGTAGCGCGAACAGACTCGATCGTACTGACCACCTGT 5'

The primer BLS-DNA-chimera all adds a restriction site for Eco RI (bold) enzyme and a Kozak consensus sequence (underlined), and the BLS-Back primer adds a restriction site for NheI enzyme (bold).

Such sequence was amplified by PCR using the pET11a-BLS-Stx2B (L5) plasmid as a template. PCR reaction was carried as described in Example 2C. The cycling profile was: 1 cycle of 94° C. for 5 minutes, 40 cycles of 94° C. for 1 minute, 55° C. for 1 minute and 74° C. for 1 minute and 1 final cycle of 74° C. for 8 minutes. The PCR product was digested with EcoRI and NheI enzymes and the pCI-neo vector was digested with EcoRI and XbaI. The EcoRI/NheI digestion was carried out as follows: 5 Units of NheI (Fermentas Inc.) in buffer Tango™ 1× (final concentration) for 4 hours at 37° C. Then, 5 Units of EcoRI (Fermentas Inc.) and buffer Tango™ were added, according to the formula V=A/8 where V is the volume of buffer to be added and A is de initial volume of the reaction. Digestion was incubated for 3 more hours at 37° C. The EcoRI/XbaI digestion was carried out with 4 Units of EcoRI and 4 Units of XbaI (Fermentas Inc.) in buffer Tango™ 2× (final concentration) for 4 hours at 37° C.

Then a ligation reaction was performed (NheI and XbaI enzymes have compatible ends) as was described in Example 2C. Ligation was transformed in *E. coli* DH5α competent cells and colonies were screened by PCR with specific primers (BLS-DNA-chimera all/BLS-Back and Forward/Reverse 5). The obtained construct was checked by sequencing. The pCI-neo-BLS-Stx2B (L5) plasmid was amplified in *E. coli* DH5α cells and further purified by "mini prep" columns (Qiagen, UK). DNA purity and concentration were assessed by spectrophotometry at 260/280 nm.

EXAMPLE 4

The pET11a-BLS-Stx2B-L10 (with the 10 amino acids linker) plasmid containing a gene with the Seq. ID. No. 6, was constructed through the following protocol:

a) To clone the codifying gene for the lumazine synthase of *Brucella* spp. (BLS), the BLS sequence was obtained by PCR amplification with specific primers from the genomic DNA of *B. abortus* and cloned in the pET11a vector (Novagen, USA). In order to develop the cassette, a directed mutagenesis was performed over the sequence codifying for the open reading frame of the lumazine synthase of *Brucella* spp. (BLS) (Laplagne et al., 2004. *Proteins* 57:820-828). Two new restriction sites were inserted in the 5' region of the BLS gene: an NsiI site in the first two codons of the 5' end, and one AflII site in the two codons comprising the 8 and 9 residues of the native amino acids sequence of BLS.

b) To insert the sequence codifying to the Stx2B protein (Seq. ID. No. 1), we designed a sequence that includes the nucleotides sequences that codify for this Stx2B protein with the site of the NsiI enzyme (underlined) at the 5' of the sequence and the site of AflII enzyme (underlined) at the 3' of the sequence plus a sequence that codify for a linker of ten amino acids (bold).

The Stx2B gene (Seq. ID. No.2) was obtained by PCR from a previously cloned sequence in pGEM-T vector as template (Capozzo et al., 2003. *Infect Immun* 71:3971-3978).

Hence, the following oligonucleotides were built to be used as primers in the PCR:

Primer forward (Seq. ID. No. 14):

5' ATCAACATGCATGCGGATTGTGCTAAAGGT 3'

Primer reverse 10 (Seq. ID. No. 15):

5' TAAAATCTTAAGAGAACCAGAACCAGAACCAGAACCAGAACCGTCAT
TATTAAACTGCAC 3'

PCR reaction was carried as described in Example 2C. The cycling profile was: 1 cycle of 94° C. for 2 minutes, 35 cycles of 92° C. for 10 seconds, 68° C. for 12 seconds and 72° C. for 30 seconds and 1 final cycle of 72° C. for 2 minutes.

The PCR product was checked using agarose gels and then purified using the Qiagen extraction Kit (Qiagen, UK).

c) The pET11a-BLS plasmid and the purified gene were digested with the NsiI and AflII restriction enzymes and ligated with DNA T4 ligase enzyme at 16° C. as described in Example 2 (C). Ligation was transformed in *E. coli* DH5α competent cells and colonies were screened by PCR with specific primers (Forward and Reverse 10). The insertion was confirmed by sequencing. The sequencing analysis showed that the first 8 amino acids of the lumazine synthase of the *Brucella* spp. were replaced by the 70 amino acids from the Stx2B protein (Seq. ID. No.1). Thus, a gene was obtained, which codes for a chimeric fusion protein called BLS-Stx2B (L10) with the Seq. ID. No. 5.

EXAMPLE 5

The pCI-Neo-BLS-Stx2B-L10 plasmid, was constructed through the following protocol:

The sequence of the gene of BLS-Stx2B (L10) Seq. ID. No. 6 cloned in pET11a vector was subcloned in the vector pCi-neo (Promega, USA). Hence, the following oligonucleotides were built to be used as primers in the PCR:

BLS-DNA-chimera all (Seq. ID. No. 16):

5' GTTTAA GAATTCGAAGGAGATACCACCATGCAT 3'

BLS-Back (Seq. ID. No. 17):

3' CGTAGCGCGAACAGACTCGATCGTACTGACCACCTGT 5'

The primer BLS-DNA-chimera all adds a restriction site for Eco RI (bold) enzyme and a Kozak consensus sequence (underlined), and the BLS-Back primer adds a restriction site for NheI enzyme (bold).

Such sequence was amplified by PCR using the pET11a-BLS-Stx2B (L10) plasmid as a template. PCR was carried out as described in Example 3. The PCR product was digested with EcoRI and NheI enzymes and the pCI-neo vector was digested with EcoRI and XbaI as described in Example 3. Then a ligation reaction was performed (NheI and XbaI enzymes have compatible ends). as described in Example 2 (C). Ligation was transformed in *E. coli* DH5α competent cells and colonies were screened by PCR with specific primers (BLS-DNA-chimera all/BLS-Back and Forward/Reverse 10). The obtained construct was checked by sequencing. The pCI-neo-BLS-Stx2B (L10) plasmid was amplified in *E. coli* DH5α cells and further purified by "mini prep" columns (Qiagen, UK). DNA purity and concentration were assessed by spectrophotometry at 260/280 nm.

EXAMPLE 6

The pET11a-BLS-Stx2B (with the 15 amino acids linker) plasmid containing a gene with the Seq. ID. No. 8 was constructed through the following protocol:

a) To clone the codifying gene for the lumazine synthase of *Brucella* spp. (BLS), the BLS sequence was obtained by PCR amplification with specific primers from the genomic DNA of *B. abortus* and cloned in the pET11a vector (Novagen, USA). In order to develop the cassette, a directed mutagenesis was performed over the sequence codifying for the open reading frame of the lumazine synthase of *Brucella* spp. (BLS) (Laplagne et al., 2004. *Proteins* 57:820-828). Two new restriction sites were inserted in the 5' region of the BLS gene: an NsiI site in the first two codons of the 5' end, and one AfI II site in the two codons comprising the 8 and 9 residues of the native amino acids sequence of BLS.

b) To insert the sequence codifying to the Stx2B protein (Seq. ID. No. 1), we designed a sequence that includes the nucleotides sequences that codify for this Stx2B protein with the site of the NsiI enzyme at the 5' of the sequence and the site of AfIII enzyme at the 3' of the sequence plus a sequence that codify for a linker of fifteen amino acids (bold).

The Stx2B gene (Seq. ID: No.2). was obtained by PCR from a previously cloned sequence in pGEM-T vector as template (Capozzo et al., 2003. *Infect Immun* 71:3971-3978).

Hence, the following oligonucleotides were built to be used as primers in the PCR:

Primer forward (Seq. ID. No. 18):

5' ATCAACATGCATGCGGATTGTGCTAAAGGT 3'

Primer reverse 15 (See ID. No. 19):

5' TAAAATCTTAAGACCAGAACCAGAACCAGAACCAGAACCAGAACCAG

AACCAGAACCGTCATTATTAAACTGCAC 3'

PCR reaction was carried as described in Example 2C. The cycling profile was: 1 cycle of 94° C. for 2 minutes, 35 cycles of 92° C. for 10 seconds, 68° C. for 12 seconds and 72° C. for 30 seconds and 1 final cycle of 72° C. for 2 minutes.

The PCR product was checked using agarose gels and then purified using the Qiagen extraction Kit (Qiagen, UK).

c) The pET11a-BLS plasmid and the purified gene were digested with the NsiI and AfIII restriction enzymes and ligated with DNA T4 ligase enzyme at 16° C., as described in example 2 (C). Ligation was transformed in *E. coli* DH5α competent cells and colonies were screened by PCR with specific primers (Forward and Reverse 15). The insertion was confirmed by sequencing. The sequencing analysis showed that the first 8 amino acids of the lumazine synthase of the *Brucella* spp. were replaced by the 70 amino acids from the feline Stx2B protein (Seq. ID. No.1). Thus, a gene was obtained, which codes for a chimeric fusion protein called BLS-Stx2B (L15) with the Seq. ID. No. 7.

EXAMPLE 7

The pCI-Neo-BLS-Stx2B-L15 plasmid, was constructed through the following protocol:

The sequence of the gene of BLS-Stx2B (L15) Seq ID No. 8 cloned in pET11a vector was subcloned in the vector pCi-neo (Promega, USA). Hence, the following oligonucleotides were built to be used as primers in the PCR:

BLS-DNA-chimera all (Seq. ID. No. 20):

5' GTTTAAGAATTCGAAGGAGATACCACCATGCAT 3'

BLS-Back (Seq. ID. No. 21):

3' CGTAGCGCGAACAGACTCGATCGTACTGACCACCTGT 5'

The primer BLS-DNA-chimera all adds a restriction site for Eco RI (bold) enzyme and a Kozak consensus sequence (underlined), and the BLS-Back primer adds a restriction site for NheI enzyme (bold).

Such sequence was amplified by PCR using the pET11a-BLS-Stx2B (L15) plasmid as a template. PCR was carried out as described in Example 3. The PCR product was digested with EcoRI and NheI enzymes and the pCI-neo vector was digested with EcoRI and XbaI as described in Example 3. Then a ligation reaction was performed (NheI and XbaI enzymes have compatible ends) as described in Example 2 (C). Ligation was transformed in *E. coli* DH5α competent cells and colonies were screened by PCR with specific primers (BLS-DNA-chimera all/BLS-Back and Forward/Reverse 15). The obtained construct was checked by sequencing. The pCI-neo-BLS-Stx2B (L15) plasmid was amplified in *E. coli* DH5α cells and further purified by "mini prep" columns (Qiagen, UK). DNA purity and concentration were assessed by spectrophotometry at 260/280 nm.

EXAMPLE 8

Purification of the BLS-Stx2B (with the 5, 10 and 15 Amino Acids Linker) Chimeras The three pet11a-BLS-Stx2Bplasmids were transformed into *E. coli* BL21 (DE3) competent cells for expression of the recombinant protein. Cells were grown in LB-broth supplemented with ampicillin, at 37° C. with agitation (250 rpm). Overnight cultures were diluted 1:100 with fresh LB-Ampicillin media and grown to reach an $OD_{600\ nm}=1$. At this point the culture was induced by adding 1 mM isopropyl β-D-thiogalactopyranoside (IPTG) (Sigma) and incubated for 3 h at 28° C. with agitation (250 rpm). The bacteria were centrifuged at 15,000 g for 20 min at 4° C. Harvested cells were resuspended in buffer 50 mM Tris-HCl, pH 8.0 and lysed by sonication.

All the Stx2B-BLS chimeras were expressed as inclusion bodies (FIG. 2A). The inclusion bodies were solubilized by overnight incubation in 8M urea, 50 mM Tris/HCl, 5 mM EDTA, pH 8 buffer at room temperature with agitation. The proteins were dialyzed against 1M urea, 50 mM Tris/HCl, 5 mM EDTA, pH 8.5 buffers with a 12-14,000 MWCO membrane (Spectrum Laboratories, Inc., Rancho Dominguez, Calif., USA). The solubilized proteins were purified by anion exchange chromatography in a Q-Sepharose (Pharmacia, GE Healthcare Life Sciences) column using a HPLC apparatus (Gilson model 320) connected to a UV/vis detector (Gilson, model 152). Elution was performed using a linear gradient between 0 and 1M NaCl in a 1M urea, 50 mM Tris/HCl, 1 mM PMSF, pH 8.5 buffer. The protein was concentrated with 10,000 MWCO Centriprep® concentration system (Millipore, Carrigtwohill, Co. Cork, Ireland). The purity of the preparations was determined by sodium dodecyl sulfate-polyacrylamide gel electrophoresis SDS-PAGE (15%, w/v) (FIG. 2 B and D) and quantified by standard methods. Protein was dialyzed against phosphate-buffered saline (PBS) previous to each immunization. The proteins had the expected molecular weight as determined by SDS-PAGE (FIG. 2D) and were recognized by anti BLS and anti Stx2 antibodies by Western Blot assay (FIG. 2C).

EXAMPLE 9

Transfection of 293T Cells with pCIneo-BLS-Stx2B L5, L10 v L15

To corroborate the correct expression of BLS-Stx2B within eukaryotic cells, 293T cells were transfected with pCI-BLS-Stx2B using PolyFect® Reagent (Qiagen Inc.). Briefly, 6×105 cells/well were grown in RPMI 1640 medium with Antibiotic-Antimycotic (AA) and 5% Fetal Bovine Serum (FBS, Natocor) in six-well culture plates at 37° C. in 5% CO2. Two μg of pCIneo-BLS-Stx2B were diluted to 100 μl with RPMI medium and 20 μl of PolyFect® reagent was added. Mixture was incubated for 10 min at room temperature in order to allow complex formation. The transfection mixture was diluted to 1 ml with RMPI medium, added to the cells and incubated for 48 h in RPMI 1640 medium with AA and 2% FBS at 37° C. in 5% CO2. After 48 hours, cells were harvested with PBS and centrifuged for 5 minutes at 1500 rpm. The cell pellet was resuspended in SDS-PAGE sample buffer (for cell lysis) and subjected to Western Blot analysis. The result of the cell lysis proteins were subjected to 15% SDS-PAGE and electro-transferred to nitrocellulose membrane. The membranes were blocked with 5% milk diluted in PBS—Tween 0.1% for 2 h at room temperature and incubated with BLS-specific antibodies (1:2,000) diluted in 3% milk, PBS—Tween 0.1% overnight at 4° C. The membranes were washed and incubated with peroxidase-conjugated rabbit anti-mouse IgG (1:3,000) (Bio-Rad Laboratories, Hercules, Calif., USA) for 2 h at room temperature. Reaction was developed with ECL solution (FIG. 3).

FIG. 3 shows that all three pCIneo-BLS-Stx2B constructs were able to express the corresponding protein in the eukaryotic cell line 293T, revealed as a specific band of the expected molecular weight (approx. 25 kDa) in the Western Blot assay.

EXAMPLE 10

Structural Analysis by Circular Dichroism

In order to evaluate the secondary structure of the purified chimeras, the Circular Dichroism (CD) signal in the far UV (200-250 nm wavelength range) was measured.

The CD spectra of BLS-Stx2B, BLS, and Stx2B in the far UV region (250-200 nm) were measured on a JASCO J-810 spectropolarimeter, in PBS, pH 7.0 buffer at 25° C., using quartz cuvettes of either 1 or 2 mm path length. Data were converted to molar ellipticity [θ] (in units of ° $cm^2$ $\mu mol_{prot}^{-}$ 1) using the theoretical molecular weight value obtained for each protein using ProtParamExPASy tools (http://web.expasy.org/protparam/).

The far UV-CD spectrum of BLS-Stx2B was shown to be practically identical to that theoretically calculated for this protein from the combination of the CD signals of isolated BLS and Stx2B. These results indicate the preservation of the secondary structure of both BLS and Stx2B in the structure of the three chimeras (FIG. 4).

EXAMPLE 11

Structural Analysis by Static Light Scattering

The average molecular weight ($M_w$) of BLS-Stx2B was determined on a Precision Detectors PD2010 light-scattering instrument connected in tandem to a high-performance liquid chromatography system including a Waters 486 UV detector and an LKB 2142 differential refractometer. In general, 200-400 μl of each BLS-Stx2B L5, L10 y L15 (0.5-1 mg/ml) was loaded on a Superdex 200 HR-10/30 column, and eluted with 50 mMTris/HCl, 0.15 M NaCl, pH 8 buffer 1M urea. The 90° light scattering and refractive index signals of the eluting material were recorded on a PC computer and analyzed with the Discovery32 software supplied by Precision Detectors. The 90° light scattering detector was calibrated using bovine serum albumin ($M_w$: 66.5 kDa) as a standard. The similarity between the resulting MW and the theoretical MW indicated the proper folded in the structure of each chimera in agreement with the quaternary structure of native BLS (FIG. 5).

EXAMPLE 12

Thermal Denaturation Analysis

The heat-induced denaturation of BLS-Stx2B L5, L10 and L15, BLS wild type and Stx2B samples in PBS pH 7.0 buffers was followed by measuring the CD signal at 222 nm of these proteins on a JASCO J-810 spectropolarimeter as a function of temperature. The samples were slowly heated by increasing the temperature with a Peltier system (Jasco). The range of temperature scanning was 25-100° C. at a speed of 4° C./min. The molar ellipticity at 222 nm was measured every 0.5° C. Thus the temperature midpoint of the thermal transition was considered as an apparent melting temperature ($T_m$). The proper folded structure of the chimeras was also supported by analysis of the thermal stability compared to the isolated STX2B and BLS modules. The thermal denaturation of these proteins was analyzed by CD spectroscopy (FIG. 6). The structure of BLS is stable up to 85° C. Above this temperature the protein cooperatively unfolds in an irreversible process with an apparent $T_m$ of 89° C. On the other hand, Stx2B remains stable up to 50° C. and then cooperatively and irreversibly unfolds with an apparent $T_m$ of 60° C.

In contrast, all the BLS-Stx2B chimeras' remains stable up to 85° C. and above this temperature the protein unfolds in a complex process. The CD signal of the chimeras decreases presumably due to an aggregation phenomena of the denatured STX2B domains in the decameric structure of the chimera that perturb the structure of the BLS modules promoting their unfolding. However, the loss of the thermal transition of STXB at 60° C. shown in all the three chimeras indicates that the molecule of BLS stabilizes the subunit of the Shiga-like B toxin delaying the denaturalization of the pentamer until 83° C.

EXAMPLE 13

$GB_3$ Binding Assay

Since the pentameric conformation of Stx2B is required for GB3 binding, a Gb3-binding ELISA assay was used to functionally confirm that the versions of the chimeric protein with peptide linkers 5, 10 or 15 amino acid long (BLS-Stx2B-L5, BLS-Stx2B-L10, and BLS-Stx2B-L15, respectively) assembled into the native holotoxin B subunit configuration. The assay was performed as previously described (Akenazi et al., 1989. *J. Clin Microbiol* 27:1145-1150). Gb3 (Matreya, State College, Pa.) dissolved in chloroform: methanol (2:1) was used to coat 96-well ELISA plates (Greiner Bio-One, Frickenhausen, Germany) at 1 μg per well. Pools of sera from BLS-Stx2B immunized mice were used as a primary antibody (diluted 1:1,000), and peroxidase-conjugated goat anti-mouse IgG (Zymed, Invitrogen, Carisbad, Calif., USA) was used as secondary antibody (dilution 1:3,000). Reaction was developed with O-phenylendiamine (Sigma, St Louis, Mo., USA) and absorbance was read at 492 nm. BLS and *E. coli* BL21 extracts were used as negative controls for non-specific binding.

A positive reaction in a dose-dependent fashion was observed for the chimeras and the recombinant Stx2 holotoxin, but not for BLS (FIG. 7). From these findings it is concluded that the B subunits on top of the BLS decamer are correctly assembled and maintain their Gb3 binding capacity in the three versions of the chimeric protein.

EXAMPLE 14

Time Course of the Antibody-Titers during the Immunization

To assess the capacity of BLS-Stx2B to improve humoral immune response compared to isolated recombinant purified Stx2B subunit (Stx2B), groups of mice were i.p. injected with the chimera having a 10 amino acid long G/S linker peptide (BLS-Stx2B-L10) or Stx2B in presence of Freund Adjuvant (FA). An Aluminum hydroxide gel (AH) suspension (1 mg/ml) was mixed with Stx2B-BLS and incubated for 30 min at room temperature with agitation. The AH-adsorbed antigen was centrifuged 10 min at 10,000 g and the pellet was resuspended in PBS.

The specific IgG antibody in sera from vaccinated mice was analyzed during more than two months. IgG titers specific to Stx2B, were elicited in both vaccinated groups (FIG. 8A). ELISA titers of the BLS-Stx2B-L10 group rose during the first three vaccinations and peaked at 14 days post the third vaccination. Meanwhile, Stx2B-immunized mice did not show specific antibody response before 45 days after the third vaccination dose, with high titer variability between individuals. At all analyzed times, the antibody titer generated by BLS-Stx2B-L10 was significantly higher than that of the Stx2B group ($P<0.005$) (FIG. 8A).

Also to evaluate BLS-Stx2B capacity to stimulate the immune system and to generate antibodies under different formulations or vaccine regimens, we immunized groups of mice with BLS-Stx2B-L10 protein with Freund Adjuvant (FA) or Aluminum hydroxide (AH), without any adjuvant, or following a DNA-protein prime-boost schedule. Serum samples were collected at different times after vaccination and titers of specific IgG were determined by ELISA. The results indicate that BLS-Stx2B chimera stimulates the immune response under all protocols tested, even without any exogenous adjuvant (FIG. 8B). On the other hand, the DNA-protein prime-boost regimen induced Stx2B specific antibodies lately (35 days after the protein boost), but reached at this time point the same titer than BLS-Stx2B-L10 with AH. The protein in absence of adjuvant induced the lowest humoral response, in terms of maximal titers and time to reach them.

Adult BALB/c mice were immunized with 3 doses of BLS-Stx2B-L10, with Freund's adjuvant (FA) (intraperitoneal, i.p.); AH (subcutaneous, s.c.) or with no adjuvant (NA) (i.p.) on days 0, 15 and 30. In the case of FA, the first dose was administrated with complete FA, the second dose with incomplete FA and the last dose without adjuvant. For AH, a suspension of 1 mg/ml was mixed with BLS-Stx2B-L10 and incubated for 30 min at room temperature with agitation. The AH-adsorbed antigen was centrifuged 10 min at 10,000 g, the pellet resuspended in PBS and inoculated into mice. Groups of mice were also i.p. immunized with BLS and Stx2B in FA. The doses of BLS and BLS-Stx2B-L10 were corrected by their molecular weights to inoculate equimolar amounts of each protein compared to that of Stx2B (the dose was equivalent to 20 μg of Stx2B).

For prime boost immunization, mice were injected with 100 μg of pCI-BLS-Stx2B-L10 on days 0, 14 and 28 by intramuscular (i.m.) route into the rear legs, followed by a final i.p. booster performed with BLS-Stx2B-L10 in incomplete FA at day 40.

Mice were anesthetized, bled by puncture of the retro-orbital plexus previous to each immunization and every 15 or 30 days to obtain serum samples.

Stx2B-specific IgG in serum samples of vaccinated mice was analyzed by ELISA assay. Briefly, 96-well MaxiSorp plates (Greiner Bio-One, Frickenhausen, Germany) were coated with 0.5 μg of purified Stx2B and blocked with 0.4% BSA PBS-Tween 0.05% for 2 h at 37° C. Then, the plates were incubated for 2 h at 37° C. with serially diluted mouse sera. After washing, the plates were incubated with peroxidase-conjugated goat anti-mouse IgG (Zymed, Invitrogen, Carisbad, Calif., USA) diluted (1:3,000) in PBS-Tween 0.05% for 1.5 h at 37° C. The plates were washed and the reaction was developed with 2 mg/ml 0-phenylenediamine (Sigma) and 0.3% $H_2O_2$ in Citrate/Phosphate buffer. Reaction was stopped with 2 M $H_2SO_4$ and absorbance at 492 nm was measured on a microtiter plate reader ASYS UVM340 (Biochrom Ltd., Cambridge, England). Results were expressed as end point titers, calculated as the reciprocal values of the last dilution with an optical density higher than the medium of pre-immune serum samples±2× Standard deviation (SD).

EXAMPLE 15

Antibody Subtyping and Antibody Affinity

BLS-Stx2B-L10 antigen induced higher anti-Stx2B specific IgG1 than IgG2a titers ($P<0.001$) for all protocols analyzed except in prime-boost schedule, in which there was not significant differences between both IgG subclasses (FIG. 9). For IgG subtyping, the ELISA was carried out as described above using peroxidase-conjugated goat anti-mouse IgG1 and IgG2a (1:1,000) (BD-Pharmigen, New Jersey, USA) as secondary antibodies.

Sera from mice immunized as in Example 14 with BLS-Stx2B-L10 formulated with FA or AH, displayed antibodies with higher affinity for Stx2B than sera from mice immunized with purified Stx2B in FA. Similar affinity results were observed in sera collected from mice immunized with BLS-Stx2B-L10 without adjuvant or in prime-boost regimens Table 1A. The Stx2B affinities of antibodies raised in immunized mice were determined by the thiocyanate elution-based ELISA. The procedure was similar to that described for the Stx2B-ELISA, with the inclusion of an extra step. After incubation with normalized concentrations of sera, plates were washed and ammonium thiocyanate (Anedra, San Fernando, Bs. As., Argentina), diluted in PBS, was added to the wells, in concentrations ranging from 0 to 4 M. The plates were allowed to stand for 15 min at room temperature before they were washed, and the assay was continued. The concentration of ammonium thiocyanate required to dissociate 50% of the bound antibody was determined. The percentage of binding was calculated as follows: $OD_{492\ nm}$ in the presence of ammonium thiocyanate×100/$OD_{492\ nm}$ in the absence of ammonium thiocyanate.

EXAMPLE 16

Neutralization Titers Against Recombinant Stx2 (rStx2)

In order to determine Stx2-neutralizing antibody titers, $1CD_{50}$ of rStx2 (670 pg of Stx2, cytotoxic dose that kills 50% of Vero cells) and serial dilutions of the experimental serum samples of mice immunized as in Example 14 were pre-incubated during 1 h at 37° C. followed by 1 h at 4° C. The mixtures were overlaid to each well containing $10^4$ Vero cells and incubated for 48 h at 37° C. in 5% $CO_2$. Cells were washed with PBS, stained with crystal violet dye and read on a microtiter plate reader (Biochrom Ltd.) with a 570 nm filter. The neutralizing activity was expressed as the reciprocal value of the highest dilution that blocked 50% of Stx2 toxicity to Vero cells.

All the sera from mice immunized with BLS-Stx2B-L10 formulated with FA showed the highest neutralizing titer ($P<0.001$). In contrast, sera from mice immunized with isolated Stx2B, even when formulated in FA, showed the lowest neutralization activity (Table 1).

TABLE 1

| | Neutralization Titer | Antibody Affinity |
|---|---|---|
| BLS-Stx2B + FA | 1508 ± 336 *** | 0.87 ± 0.17 * |
| BLS-Stx2B + AH | 178 ± 86 | 1.01 ± 0.11 * |
| BLS-Stx2B N/A | 104 ± 66 | 0.52 ± 0.10 |
| Prime Boost | 203 ± 92 | 0.62 ± 0.14 |
| Stx2B + FA | 60 ± 48 | 0.41 ± 0.05 |

*** Significantly different from other groups
* Significantly different from Stx2B + Freund's adjuvant Table 1: Antigen Affinity and Neutralization Capacity of Sera from Immunized Mice Antibody affinity was represented as molar ammonium thiocyanate concentrations required to dissociate 50% of the bound antibodies (in ELISA test). Results are expressed as the mean±SEM of 4-6 mice/group.

Sera from immunized mice (45 days post last immunization) were pre-incubated in vitro with rStx2 and its toxicity assayed onto Vero cells as detailed in Materials and Methods. Each value represents the mean±SEM of 4-6 mice/group. * $P<0.05$ vs. Stx2B+FA group; *** $P<0.001$ vs. all other vaccination protocols.

EXAMPLE 17

Cross-reactivity of Mouse Sera

For this purpose supernatants from human-isolated EHEC strains producing Stx2, or Stx2c or Stx2d variants were incubated with sera from mice immunized with BLS-Stx2B-L10+FA or Stx2B+FA, as in Example 14 and toxicity on Vero cells was evaluated. We also evaluated neutralization capacity against recombinant Stx1 (rStx1). Sera from mice immunized with BLS-Stx2B-L10 strongly neutralized wild Stx2 and its variants, and also rStx1. In sharp contrast, only the serum sample harvested from one out of six mice immunized with purified Stx2B was able to weakly neutralized wild Stx2, and none of them neutralized Stx2 variants or rStx1 (Table 2).

TABLE 2

| | BLS-Stx2B + FA | Stx2B + FA |
|---|---|---|
| Stx2 | 2461 ± 522 | 42 ± 42 |
| Stx2c | 1731 ± 346 | 0 |
| Stx2d | 1740 ± 386 | 0 |
| Stx1 | 966 ± 486 | 0 |

Table 2: Neutralization titers against purified rStx1, wild Stx2 and its variants. Sera from immunized mice with Stx2B or BLS-Stx2B-L10, both formulated with FA (45 days post last immunization), were incubated in vitro with 1CD50 of each Stx and toxicity assayed onto Vero cells and the results expressed as detailed in Materials and Methods. Each value represents the mean±SEM of 6 mice/group.

EXAMPLE 18

Protection of Immunized Mice Against rStx2 Challenge: Ex Vivo rStx2 Neutralization Activity For the ex vivo assay, 2.2 ng/mice of rStx2 (one lethal dose 100%, $1LD_{100}$) was pre-incubated with sera from mice immunized as in Example 14 for 1 h at 37° C. and 1 h at 4° C. The mixture was inoculated intravenously (i.v.) into naive adult BALB/c mice and survival was observed. This dose of rStx2 leads to 100% mortality within 96 h after injection. As indicated in FIG. 10A pre-incubation of rStx2 with sera harvested from mice immunized with BLS-Stx2B-L10 under different protocols fully abrogated rStx2 toxicity, while sera from Stx2B-vaccinated mice did not prevent rStx2-toxicity.

EXAMPLE 19

Intravenous Challenge with rStx2 and Long-Term Response

Mice Immunized as in Example 14 were challenged by i.v. inoculation with $1LD_{100}$ of rStx2 50 days after the last immunization. FIG. 10B shows that 100% of the BLS-Stx2B-L10 vaccinated mice and 33% of the Stx2B vaccinated mice survived the rStx2 lethal challenge. According to the rStx1 dose used, 0% of the animals immunized with BLS or non-immunized mice survived the challenge (FIG. 10B).

Sera from surviving BLS-Stx2B immunized mice were long term harvested to study the duration of specific antibody response (FIG. 11 A). All BLS-Stx2B regimens induced a long-lasting immune response evaluated as ELISA anti-Stx2 antibodies. Mice were re-challenged with $2LD_{100}$ (4.4 ng/mice) of rStx2 8 months after the last dose and with 3 LD100 (6.6 ng/mice) 10 months after the last dose (FIG. 11B). All BLS-Stx2B-L10 vaccinated mice survived the challenged with 2LD100 at eight months after the last immunization dose, and the challenge with 3 LD100 at 11 months after the last immunization dose.

EXAMPLE 20

Protective Capacity of Antibodies Raised by Immunization with One Dose of bls-stx2b-l10

To further analyze the protective capacity of antibodies raised by immunization with the BLS-Stx2B-L10 protein, adult BALB/c mice were immunized with one dose of BLS-Stx2B-L10 formulated in Aluminum hydroxide (the dose was equivalent to 20 μg of Stx2B). An Aluminum hydroxide gel (AH) suspension (1 mg/ml) was mixed with BLS-Stx2B-L10 and incubated for 30 min at room temperature with agitation. The AH-adsorbed antigen was centrifuged 10 min at 10,000 g and the pellet was resuspended in PBS. Serum samples were collected at different times after vaccination and titers of specific IgG were determined by ELISA. Stx2B-specific IgG in serum samples of vaccinated mice was analyzed by ELISA assay as described in Example 14.

FIG. 12 shows that one dose of BLS-Stx2B-L10 is enough to develop a specific-IgG humoral response.

To test de protective capacity of the immune response, mice were challenged with $1LD_{100}$ of rStx2 one month post-immunization. FIG. 13 A shows that 100% of the BLS-Stx2B-L10 vaccinated mice survived the rStx2 lethal challenge while 0% of the non-immunized mice survived the challenge.

Surviving mice were re-challenged with $3LD_{100}$ and $5LD_{100}$ at 2 months post-immunization and 4 months post-immunization, respectively. FIG. 13 B and C shows that all mice were able to survive both challenges with high doses of rStx2, indicating the high protective capacity of the antibodies raised by immunization with BLS-Stx2B-L10.

The invention claimed is:

1. A chimeric protein, comprising from amino-terminus to carboxy-terminus a Shiga toxin 2 subunit B (Stx2B) monomer, a peptide linker, and a *Brucella* lumazine synthase (BLS) monomer, wherein:
   - the Stx2B monomer comprises a peptide having at least 95% identity to the amino acid sequence of SEQ ID NO:1,
   - the BLS monomer comprises a peptide having at least 95% identity to amino acids 9-158 of SEQ ID NO:9, and
   - the chimeric protein is capable of: (a) binding to globotriaosylceramide (Gb3) and (b) eliciting cross-reactive antibodies against Shiga toxin 1 (Stx1) and Shiga toxin 2 (Stx2) and/or against allelic variants of Stx2.

2. The chimeric protein of claim 1, wherein the peptide linker ranges from 2 amino acids to 20 amino acids in length.

3. The chimeric protein of claim 2, wherein the peptide linker comprises a Gly-Ser flexible linker.

4. The chimeric protein of claim 3, wherein the Gly-Ser flexible linker is comprised of amino acids 73-77 of SEQ ID NO:3, amino acids 73-82 of SEQ ID NO:5, or amino acids 73-87 of SEQ ID NO:7.

5. The chimeric protein of claim 1, wherein the Stx2B monomer comprises or consists of the amino acid sequence of SEQ ID NO:1.

6. The chimeric protein of claim 1, wherein the BLS monomer comprises or consists of amino acids 9-158 of SEQ ID NO:9.

7. The chimeric protein of claim 1, wherein the chimeric protein has at least 95% identity to the amino acid sequence of any one of SEQ ID NOS:3, 5, and 7.

8. The chimeric protein of claim 1, wherein the chimeric protein comprises or consists of the amino acid sequence of any one of SEQ ID NOS:3, 5, and 7.

9. A protein oligomeric complex, comprising a dimer of pentamers of the chimeric protein of claim 1.

10. A pharmaceutical composition, comprising the protein oligomeric complex of claim 9 and a pharmaceutically acceptable carrier.

11. The pharmaceutical composition of claim 10, further comprising an adjuvant.

12. The pharmaceutical composition of claim 11, wherein the adjuvant is selected from the group consisting of Freund's adjuvant (FA), an aluminum compound, a liposome, a non-ionic block polymer, a saponin, and dimethyl dioctadecylamonium bromide (DDA).

13. The pharmaceutical composition of claim 11, wherein the adjuvant is an aluminum hydroxide gel.

14. The pharmaceutical composition of claim 11, wherein the adjuvant is Freund's adjuvant.

15. A method for producing a neutralizing antibody against Shiga toxin 2 subunit B (Stx2B), the method comprising the steps of:
   - (a) administering to a mammal an effective amount of the pharmaceutical composition of claim 10 for a time sufficient to elicit neutralizing antibodies against Stx2B, and
   - (b) obtaining from the mammal neutralizing antibodies and/or cells capable of producing the neutralizing antibodies.

16. The method claim 15, wherein the pharmaceutical composition further comprises an adjuvant.

17. The method of claim 15, wherein the protein oligomeric complex of the pharmaceutical composition is comprised of a chimeric protein having at least 95% identity to the amino acid sequence of any one of SEQ ID NOS:3, 5, and 7.

18. The method of claim 15, wherein the protein oligomeric complex of the pharmaceutical composition is comprised of a chimeric protein comprises or consists of the amino acid sequence of any one of SEQ ID NOS:3, 5, and 7.

19. The method of claim 15, wherein the pharmaceutical composition elicits cross-neutralizing antibodies against Shiga toxin 1 (Stx1) and Shiga toxin 2 (Stx2).

20. The method of claim 15, wherein the pharmaceutical composition elicits cross-neutralizing antibodies against Shiga toxin 2 (Stx2) and allelic variants thereof.

21. The method of claim 20, wherein the antibodies cross-neutralize Stx2 allelic variant Stx2c, Stx2d, or both.

22. A method of inducing a protective immune response against hemolytic-uremic syndrome (HUS), comprising administering to a mammalian subject an effective amount of the pharmaceutical composition of claim 10 for a time sufficient to elicit a protective immune response.

23. The method claim 22, wherein the pharmaceutical composition further comprises an adjuvant.

24. The method of claim 22, wherein the protein oligomeric complex of the pharmaceutical composition is comprised of a chimeric protein having at least 95% identity to the amino acid sequence of any one of SEQ ID NOS:3, 5, and 7.

25. The method of claim 22, wherein the protein oligomeric complex of the pharmaceutical composition is comprised of a chimeric protein comprises or consists of the amino acid sequence of any one of SEQ ID NOS:3, 5, and 7.

* * * * *